US011541329B2

(12) United States Patent
Seabrook et al.

(10) Patent No.: US 11,541,329 B2
(45) Date of Patent: Jan. 3, 2023

(54) LIQUID CARBON DIOXIDE AND COSOLVENT BIOMASS EXTRACTION METHOD AND SYSTEM

(71) Applicant: Vitalis Extraction Technology Inc., Kelowna (CA)

(72) Inventors: James Anthony Seabrook, West Kelowna (CA); Kiran Dayaram, Kelowna (CA); Spencer Hugh Martin, Kelowna (CA); Raymond Lyle Brown, Kelowna (CA); Sean Cameron Demers, Kelowna (CA)

(73) Assignee: Vitalis Extraction Technology Inc., Kelowna (CA)

( * ) Notice: Subject to any disclaimer, the term of this patent is extended or adjusted under 35 U.S.C. 154(b) by 0 days.

(21) Appl. No.: 17/587,549

(22) Filed: Jan. 28, 2022

(65) Prior Publication Data
US 2022/0249977 A1   Aug. 11, 2022

Related U.S. Application Data

(60) Provisional application No. 63/143,284, filed on Jan. 29, 2021.

(51) Int. Cl.
*B01D 11/02* (2006.01)
*C07C 37/82* (2006.01)
*B01J 3/00* (2006.01)

(52) U.S. Cl.
CPC ...... *B01D 11/0203* (2013.01); *B01D 11/0288* (2013.01); *B01J 3/008* (2013.01); *C07C 37/82* (2013.01)

(58) Field of Classification Search
CPC .. B01D 11/0203; B01D 11/0288; B01J 3/008; C07C 37/82
See application file for complete search history.

(56) References Cited

U.S. PATENT DOCUMENTS

| | | | |
|---|---|---|---|
| 6,759,065 B1 | 7/2004 | Ruijten | |
| 6,908,557 B2 | 6/2005 | Chordia et al. | |
| 9,044,390 B1 | 6/2015 | Speier | |
| 9,199,960 B2 | 12/2015 | Ferri | |
| 9,649,349 B1 | 5/2017 | Tucker et al. | |
| 9,744,200 B1 | 8/2017 | Tucker et al. | |
| 10,471,113 B1* | 11/2019 | Castillo ............. | B01D 11/0273 |
| 10,478,747 B2 | 11/2019 | Ko | |
| 10,557,105 B1 | 2/2020 | Tran et al. | |
| 10,888,595 B2 | 1/2021 | Rivas | |
| 10,982,899 B1 | 4/2021 | Gelardi | |
| 2002/0139752 A1* | 10/2002 | Berger .................. | B01D 15/40 |
| | | | 436/178 |
| 2015/0283477 A1* | 10/2015 | Chess ................ | B01D 11/0203 |
| | | | 202/168 |
| 2017/0368022 A1* | 12/2017 | Sorbo ................ | B01D 11/0273 |

(Continued)

*Primary Examiner* — Bradley R Spies
*Assistant Examiner* — Jeannie McDermott

(57) ABSTRACT

Method and system for the extraction of oils from a biomass with a liquid carbon dioxide using cosolvent. The system and method can be used to extract cannabinoids from cannabis biomass by cryogenically freezing the biomass and exposing the cannabis biomass to sub-cooled liquid carbon dioxide and capturing a first high-terpene extract fraction, and then exposing the cannabis biomass with a mixture of superfluid carbon dioxide and a cosolvent to capture a high cannabinoid second fraction.

20 Claims, 28 Drawing Sheets

(56) References Cited

U.S. PATENT DOCUMENTS

| | | | |
|---|---|---|---|
| 2018/0112896 A1* | 4/2018 | James | F25B 7/00 |
| 2019/0153484 A1* | 5/2019 | Bray | C12P 7/22 |
| 2021/0040414 A1* | 2/2021 | Tran | C11B 1/04 |
| 2021/0069610 A1* | 3/2021 | Pierce | B01D 11/0265 |

* cited by examiner

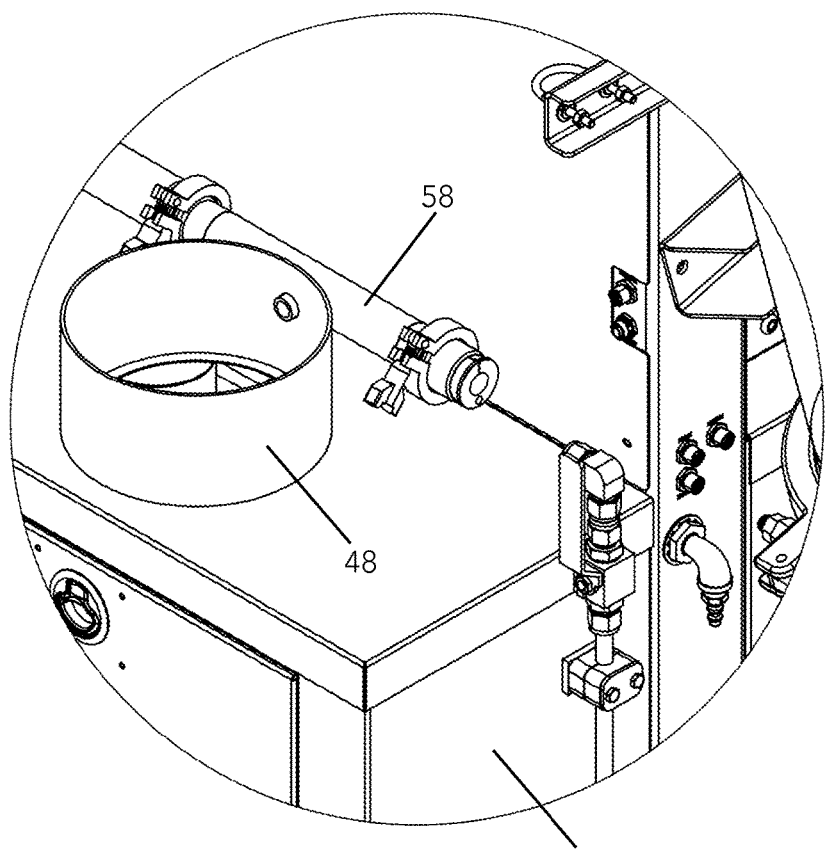
Figure 9B
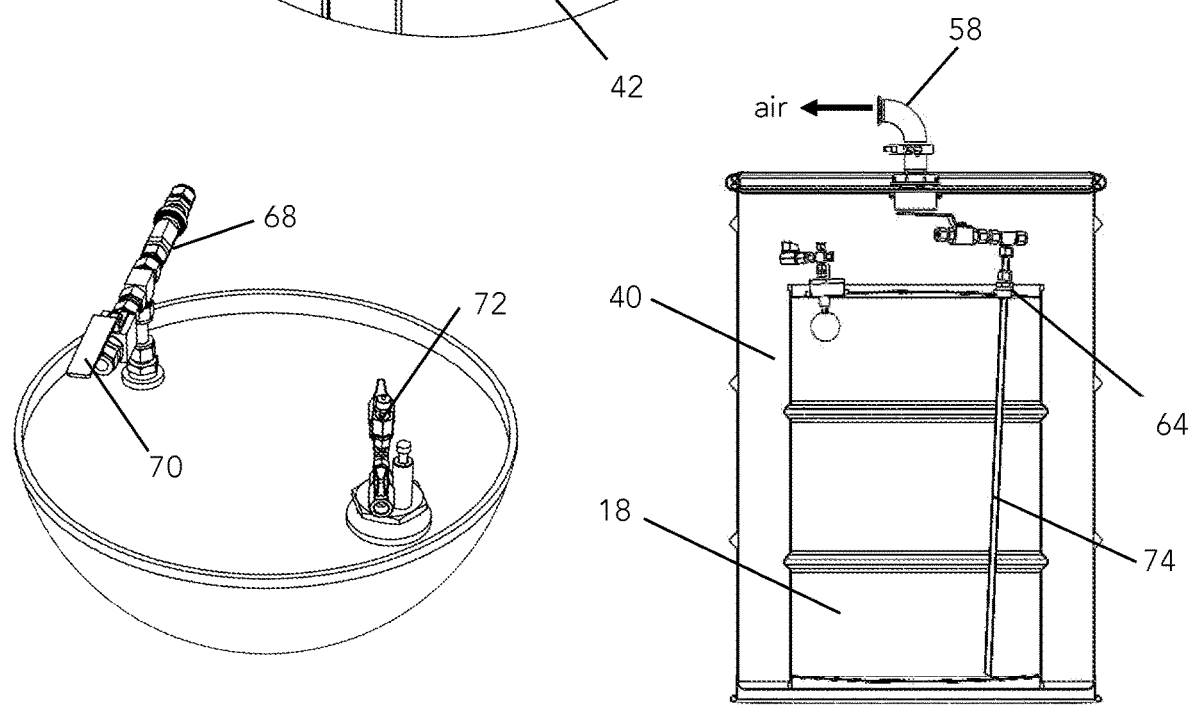
Figure 9C
Figure 9D

LIQUID CARBON DIOXIDE AND COSOLVENT BIOMASS EXTRACTION METHOD AND SYSTEM

CROSS-REFERENCE TO RELATED APPLICATIONS

This application claims priority to U.S. provisional patent application U.S. 63/143,284 filed 29 Jan. 2021, which is hereby incorporated by reference herein in its entirety.

FIELD OF THE INVENTION

The present invention pertains to a cosolvent system and method for liquid carbon dioxide superfluid extraction of biomass. The present invention also pertains to a cryogenic pre-freezing and cooling process in a method for extracting oils from biomass using a cosolvent liquid carbon dioxide extraction. The present invention also pertains to a process for controlled cosolvent addition and removal from a liquid carbon dioxide extraction system.

BACKGROUND

Carbon dioxide ($CO_2$) extraction, separation, and purification of plant material has become an important commercial and industrial process due to the ease of use of $CO_2$ as a solvent in chemical separation, as well as its low toxicity, non-flammability, low cost, and low environmental impact compared to other solvents. The relatively low temperature of the process and the stability of $CO_2$ also allows many compounds to be extracted from biomass with little damage or denaturing. In addition, the solubility of many extracted compounds in $CO_2$ varies with pressure, permitting selective separations.

Carbon dioxide behaves as a gas in air at standard temperature and pressure (STP), and its physical state can be tuned by controlling temperature and pressure in a closed system or closed environment. $CO_2$ extraction can be used, for example, for analytical purposes, decaffeination or component removal from a plant material, in winterization to separate fats and waxes from plant extracts, and for separating and collecting desired products from plant products such as terpenes and essential oils. Compared to other forms of extraction and separation, the use of carbon dioxide is also advantageous because the $CO_2$ solvent can be easily separated from the extract by evaporation. By using liquid $CO_2$ as the solvent in winterization, the solvent separation process is simplified, as $CO_2$ evaporates at a much lower temperature than the compounds of interest and therefore can be easily evaporated by raising the temperature or lowering the pressure of the mixture. In closed systems and in pressure controlled environments where $CO_2$ is held at conditions in or around the critical point or saturation line, such as in a subcritical extraction, both liquid and vapour $CO_2$ can exist simultaneously in the system, whereas in high pressure systems such as those required to maintain $CO_2$ in a liquid state, the solvent needs to be maintained at relatively high pressures.

The International Council for Harmonisation of Technical Requirements for Pharmaceuticals for Human Use (ICH, "Q3C guideline") and the United States Food and Drug Administration (FDA) have developed guidelines on residual solvents which are allowed in low levels as impurities in pharmaceutical products. Class 3 solvents in the Q3C guideline are solvents that are less toxic and of lower risk to human health and are not known to be a human health hazard at the level accepted in pharmaceutical products in accordance with the guideline. The class 3 solvents include acetic acid, acetone, anisole, 1-butanol, 2-butanol, butyl acetate, tertbutyl methyl ether, dimethyl sulfoxide, ethanol, ethyl acetate, ethyl ether, ethyl formate, formic acid, n-heptane, isobutyl acetate, isopropyl acetate, methyl acetate, 3-methyl-1-butanol, methyl ethyl ketone, 2-methyl-1-propanol, pentane, 1-pentanol, 1-propanol, 2-propanol, propyl acetate, and triethylamine. The Q3C guideline considers that amounts of class 3 solvents of 50 mg per day or less would be acceptable without justification, and higher amounts may also be acceptable provided they are realistic in relation to manufacturing capability and good manufacturing practice (GMP). Class 2 solvents, which are higher in toxicity than class 3 solvents, may also be used with caution, including methanol, providing that the permitted daily exposure (PDE) limits are carefully maintained. In liquid carbon dioxide cosolvent systems that use $CO_2$ as the primary solvent, class 3 solvents (or class 2 solvents with appropriate control) can be used as cosolvents to provide process improvements such as, for example, improved separation, shorter process times, and higher process volumes. However, many of the class 3 solvents are flammable, and if not stored and handled properly, can pose a serious threat to health and safety. In particular, avoiding contact with skin and eyes, keeping the solvent away from incompatibles such as oxidizing agents, acids, alkalis, moisture, as well as open flames, sparks, and heat, it is important to maintaining a safe workplace and in instrument design.

In one example of cosolvent use with liquid carbon dioxide, U.S. Pat. No. 6,908,557B2 to Chordia et al. describes a method and device for a chromatography column at high pressure which uses a compressed fluid, such as $CO_2$, combined with one or more solvents to collect a desired compound. The desired compound or compounds eluted from the chromatographic column are detected using a detector and based on detector signal response, the flow stream is directed to one or more collection chambers using a switching valve.

There remains a need for a liquid carbon dioxide cosolvent system and method that can be integrated with a liquid carbon dioxide extraction system for controlled collection of compounds of interest from biomass or media containing compounds of interest using liquid carbon dioxide and a cosolvent.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a method for extracting oils from biomass comprising sub-cooled liquid carbon dioxide and a cosolvent. Another object of the present invention is to provide a cosolvent system and method that can be safely integrated and interlocked with a liquid carbon dioxide extraction system for controlled collection of compounds of interest. Another object of the present invention is to provide a cosolvent system for controlling the process conditions of cosolvent use in a liquid carbon dioxide superfluid extraction system and allow for in-line and in-process recovery of fractions and recycling of solvent and cosolvent.

In an aspect there is provided a method for biomass extraction comprising: in a cryogenic cooling step, cooling the biomass with liquid carbon dioxide to a temperature of 0° C. or less at a pressure of less than 500 psi; in a monosolvent extraction step, extracting the biomass with liquid carbon dioxide monosolvent while maintaining the temperature of the biomass at 0° C. or less to obtain one or more monosolvent fractions; in a cosolvent extraction step, extracting the biomass with liquid carbon dioxide and a cosolvent to obtain one or more cosolvent fractions; and evaporating the monosolvent fractions and cosolvent fractions to remove the carbon dioxide and obtain an extractant oil.

In an embodiment the liquid carbon dioxide in the monosolvent extraction step and the cosolvent extraction step is in a subcritical state or supercritical state.

In another embodiment in the cooling step, the biomass is cooled at a pressure of 400 psi or less.

In another embodiment prior to the cooling step the biomass is dry, fresh, or fresh frozen.

In another embodiment at least one of the monosolvent extraction step and the cosolvent extraction step are carried out at a temperature of −10 C or less.

In another embodiment the cooling step is performed under isobaric conditions.

In another embodiment the cosolvent extraction step is carried out at a pressure of between 1500-2200 psi.

In another embodiment the cosolvent in the cosolvent extraction step is between 0.1-10% by volume in sub-cooled liquid carbon dioxide.

In another embodiment the method further comprises dewaxing the extractant oil by one or more of filtration, dewaxing, and nanofiltration.

In another embodiment, the method further comprises desolvation of the cosolvent fractions.

In another embodiment the method further comprises reclaiming the cosolvent.

In another embodiment the method further comprises, after the cosolvent extraction step, remediating the biomass by treatment with $CO_2$ monosolvent to remove residual cosolvent.

In another embodiment the remediated biomass has a cosolvent residual of less than 5000 ppm when removed from the extraction column.

In another embodiment the cosolvent is ethanol, ethyl acetate, isopropyl alcohol, acetone, or a combination thereof.

In another embodiment in the cosolvent extraction step the cosolvent is added in an isocratic, step, or linear regime to the liquid carbon dioxide.

In another aspect there is provided a method for extracting molecules from biomass comprising: in a monosolvent extraction step, extracting cryogenically frozen biomass at a temperature of 0° C. or less with liquid carbon dioxide monosolvent while maintaining the temperature of the biomass at 0° C. or less to obtain one or more monosolvent fractions; in a cosolvent extraction step, extracting the biomass with liquid carbon dioxide and a cosolvent to obtain one or more cosolvent fractions; and evaporating the monosolvent fractions and cosolvent fractions to remove the carbon dioxide and obtain an extractant oil.

In an embodiment the method further comprises, before the monosolvent extraction step, a cryogenic cooling step comprising cooling the biomass with liquid carbon dioxide to a temperature of 0° C. or less at a pressure of less than 500 psi.

In another embodiment prior to the monosolvent extraction step the biomass is dry, fresh, or fresh frozen.

In another embodiment at least one of the monosolvent extraction step and the cosolvent extraction step are carried out at a temperature of −10 C or less.

In another embodiment the monosolvent extraction step is carried out at a pressure of between 400-800 psi and the cosolvent extraction step is carried out at a pressure of between 1500-2200 psi.

In another aspect there is provided a superfluid cosolvent system comprising: a solvent pump for receiving and pressurizing solvent; high pressure fluid lines connecting the solvent pump to a superfluid extraction system; a collection vessel comprising a collection vessel intake for receiving high pressure supercritical fluid and extractant from the superfluid extraction system, a collection vessel outlet for transferring extractant out of the collection vessel, a depressurizing valve, and an exhaust vent line for directing gas and vapor away from the collection vessel.

In an embodiment the system further comprises a control system for controlling depressurization of the depressurizing valve.

In another embodiment the control system further controls solvent transfer from the solvent pump to the superfluid extraction system.

In another embodiment the system further comprises a pump enclosure for the solvent pump.

In another embodiment the system further comprises a solvent supply tank fluidly connected to the solvent pump.

In another embodiment the system further comprises an integrated spill and vapour management vented containment device.

In another embodiment the system further comprises a plurality of exhaust vent lines and a liquid trap connected to the plurality of exhaust vent lines to capture vaporized solvent.

In another embodiment the system further comprises a transfer tank for receiving extractant from the collection vessel.

In another aspect there is provided a method for extracting oil from a biomass with a superfluid, the method comprising: putting the biomass into an extraction column; providing a mixture of superfluid and cosolvent into the extraction column to extract extractant oils from the biomass; directing superfluid, cosolvent, and extractant from the extraction column to a superfluid separator to remove the superfluid; directing extractant and cosolvent from the separator to a collection vessel under high pressure; depressurizing the collection vessel; and collecting the extractant and cosolvent.

In an embodiment the method further comprises reclaiming the cosolvent.

In another embodiment the method further comprises recycling the superfluid removed from the separator.

In another embodiment the method further comprises secondary processing of the extractant and cosolvent to remove the cosolvent.

In another embodiment the method further comprises chromatographic pre-analysis of the cannabis biomass to determine the total available oil for extraction.

In another embodiment the chromatographic pre-analysis is HPLC, GCMS, TLC, or HPLC and GCMS.

In another embodiment the method further comprises exposing the biomass to a monosolvent superfluid $CO_2$.

In another embodiment the monosolvent superfluid $CO_2$ substantially remediates the biomass from residual cosolvent.

In another embodiment the remediated biomass has a cosolvent residual of less than 5000 ppm when removed from the extraction column.

In another embodiment the method further comprises directing the extractant and cosolvent to a secondary processing unit.

In another aspect there is provided a method for extracting cannabinoids from a cannabinoid-containing biomass comprising: exposing the biomass to monosolvent superfluid $CO_2$ and capturing a first extract fraction; and exposing the biomass with a mixture of superfluid $CO_2$ and a cosolvent and capturing a second fraction comprising high concentration of cannabinoids.

In an embodiment the second extract fraction contains at least 50% of available cannabinoids from the biomass.

In another embodiment the cosolvent comprises a class 3 solvent.

In another embodiment the cosolvent is ethanol, ethyl acetate, isopropyl alcohol, acetone, or a combination thereof.

In another embodiment the cosolvent is 0.1-10.0% by mass of the superfluid $CO_2$.

In another embodiment the superfluid $CO_2$ is subcritical $CO_2$ or supercritical $CO_2$.

In another embodiment the first extract fraction comprises a high concentration of terpenes.

In another embodiment the method further comprises secondary processing of the second fraction to remove the cosolvent.

In another embodiment the secondary processing of the second fraction to remove the superfluid $CO_2$ and cosolvent results in an extract comprising more than 70% cannabinoids.

In another embodiment each of the first fraction and second fraction are independently collected for bulk secondary processing.

In another embodiment the method further comprises chromatographic pre-analysis of the biomass to determine the total available cannabinoids and total available terpenoids.

In another embodiment the chromatographic pre-analysis is one or more of high performance liquid chromatography (HPLC), gas chromatography mass spectrometry (GCMS), and thin layer chromatography (TLC).

In another embodiment the method further comprises, after collecting the second fraction, exposing the biomass with a monosolvent superfluid $CO_2$ and capturing a third fraction.

In another embodiment the monosolvent superfluid $CO_2$ substantially remediates the biomass from residual cosolvent.

In another embodiment the remediated biomass has a cosolvent residual of less than 5000 ppm when removed from the extraction column.

In another embodiment the method is adjusted based on total available terpenes and cannabinoids.

In another embodiment the superfluid pressure and temperature, cosolvent injection rate, and column linear velocity over the duration of the extraction process reduce co-extraction of undesirables.

In another aspect there is provided a superfluid extraction system comprising: an extraction column for receiving biomass; a separator fluidly connected to the extraction column; a superfluid management system comprising a superfluid pump for pressurizing superfluid, a superfluid reservoir for storing and supplying superfluid, a supercritical fluid condenser, and a heat exchanger; a cosolvent pump for receiving and pressurizing cosolvent; a collection vessel comprising a collection vessel intake for receiving high pressure supercritical fluid and extractant from the superfluid extraction system, an outlet for transferring extractant out of the collection vessel, a depressurizing valve, and an exhaust vent line for directing gas and vapor away from the collection vessel; and high pressure superfluid supply lines fluidly connecting the superfluid management system to the extraction column, separator, cosolvent pump, and collection vessel.

In an embodiment the system further comprises a control system for controlling superfluid pressure in the superfluid extraction system.

In another embodiment the separator is a cyclone separator.

In another embodiment the system further comprises a chemical sensor for detecting chemical species downstream the extraction column.

In another embodiment the extraction column is a chromatography column.

In another embodiment the system further comprises a cosolvent supply tank.

In another embodiment the system further comprises one or more temperature sensor, pressure gauge, pressure release valve, and flow sensor.

In another embodiment the system further comprises more than one extraction column.

In another embodiment the system further comprises more than one separator.

In another embodiment the system further comprises an integrated spill and vapour management vented containment device.

BRIEF DESCRIPTION OF THE FIGURES

For a better understanding of the present invention, as well as other aspects and further features thereof, reference is made to the following description which is to be used in conjunction with the accompanying drawings, where:

FIG. 9B is a close up view of vent detail D in FIG. 9A;

FIG. 9C is a close up view of cosolvent feed tank port connections from detail E in FIG. 9A;

FIG. 9D is a side cross-sectional view of a cosolvent feed tank nested in a secondary containment tank;

DETAILED DESCRIPTION OF THE INVENTION

Figure 1:
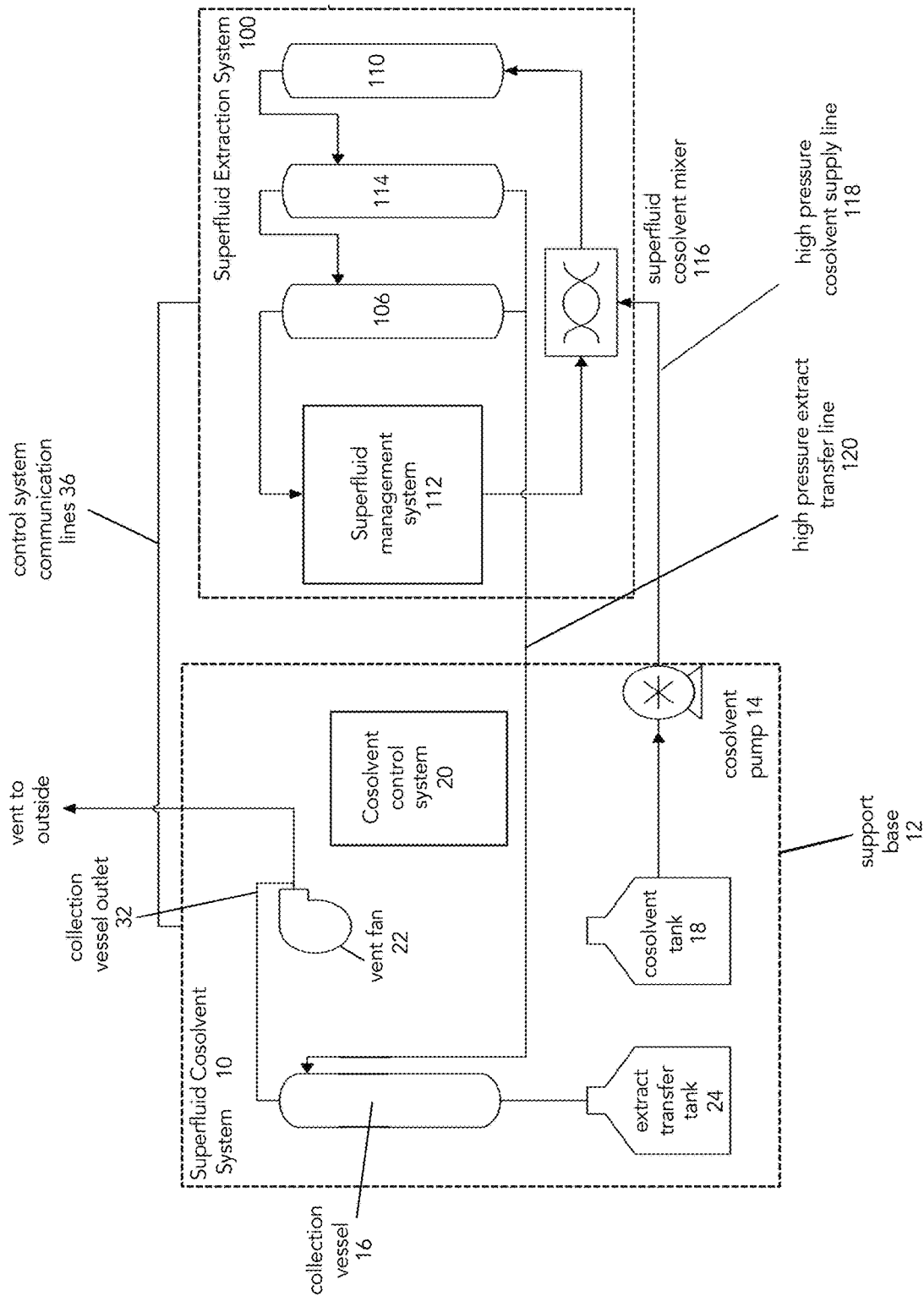
FIG. 1 is a system schematic of a superfluid cosolvent system connected with a superfluid extraction system.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or element(s) as appropriate.

As used herein, the terms "subcritical fluid" and "subcooled fluid" refer to a fluid which is compressed and maintained below its critical temperature in the liquid state. Subcritical fluids can exist at saturation conditions where there are two or three distinct phases including solid, liquid, and vapor. Subcritical fluids are used herein in their liquid state. Subcritical fluid states vary along a range of temperatures and pressures and are unique to each fluid, which includes solvents, liquids, and the same with dissolved and/or emulsified materials therein. Generally subcritical conditions for carbon dioxide, for example, exist between 0.6 MPa (80 psi) and 70 MPa (10,000 psi), above the saturation curve, and always below about 31.2 degree centigrade.

As used herein, the term "supercritical fluid" refers to a fluid wherein the fluid can exist in a supercritical condition with no clear distinction between vapour and liquid states, or combination of both vapour and liquid states. In a supercritical state, the fluid is at a temperature and pressure above its critical point, where distinct liquid and gas phases do not exist, but below the pressure required to compress it into a solid. Generally supercritical conditions for carbon dioxide, for example, exist above 7.38 MPa (1070 psi) and above 31.1 degrees centigrade (88° F.).

As used herein the term "superfluid" refers to a fluid with near-zero or zero viscosity which flows with minimal loss of kinetic energy. The term "superfluid" encompasses both supercritical fluids and subcritical fluids and represents the properties of a class of fluids which can exist independently or as a solution at supercritical conditions.

As used herein, the term "superfluid extraction" (SFE) refer to the process of separating a desirable extractant from another material where supercritical fluid or subcritical fluid is the primary extracting solvent. Because the physical properties of supercritical fluids and subcritical fluids are close to those of liquids and their transport properties are close to those of gases, supercritical fluids and subcritical fluids can penetrate into a porous solid material more effectively than liquid solvents. Subcritical fluids can also be used at slightly lower temperatures and pressures. Moreover, after extraction, the solvent can be easily separated from the extract by decreasing the pressure and evaporating the solvent. In an SFE extraction from plants, the matrix is usually solid matrix, but can also be liquid. SFE can be used, for example, for analytical purposes, decaffeination or component removal from a plant material, or collecting desired product such as terpenes or essential oils. The conditions for extraction of oil and other desirable components from plant material is dependent on temperature, pressure, solvent to feed ratio and flow rate, superfluid used, and conditions for extraction vary based on the plant material used. Carbon dioxide ($CO_2$) is the most used supercritical/subcritical fluid and is referred to herein as the example main solvent, however it is understood that other superfluids can also be used.

As used herein, the term "cryogenic" refers to a temperature of 0° C. or less.

Described herein is a method for extracting oils from biomass using carbon dioxide and cosolvent superfluid extraction. Also described herein is a method of extraction of biomass using a cryogenic pre-freezing step which freezes the water in the biomass prior to extraction. This method is particularly useful with fresh, fresh-frozen, or limitedly dried biomass, which has so far been believed to be challenging due to the miscibility of liquid $CO_2$ and water. In the present method, a preliminary step of cryogenic freezing of the biomass, which can be fresh biomass, and maintaining the process conditions below 0° C. reduces or eliminates the extraction of water in subsequent extraction steps. The cryogenic pre-freezing step can be followed by monosolvent or monosolvent and cosolvent extraction to provide the desired biomass oils. In the extraction of oils from cannabis, for example, this process allows for the extraction of terpenes and oils directly from a field product where no drying is required.

Also described herein is a superfluid cosolvent system which can be safely connected to a superfluid extraction system to provide controlled delivery and removal of cosolvent. Also described herein is a method for extracting oils from biomass comprising a first cryofreezing or cooling step of the biomass followed by superfluid solvent and cosolvent extraction. The presently described superfluid cosolvent system and method can decrease overall process time on carbon dioxide ($CO_2$) superfluid extraction machines and improve compound selectability while maintaining product quality.

The carbon dioxide superfluid extraction process is considered to be a non-destructive extraction technique for extracting active plant biopharmaceutical from plant biomass, and in particular major and minor cannabinoids, as well as terpenes, from cannabis biomass. With the controlled addition of cosolvent to a superfluid extraction system, cosolvent conditions can be altered in addition to other process conditions to provide greater variation in process control for extraction of components from biomass. The present cosolvent system and method can also reduce cosolvent use during superfluid extraction by effectively isolating biomass components in a stepwise extraction, controlling the injection volume of cosolvent, and by cosolvent reclamation and recycling.

FIG. 1 is a system schematic of a superfluid cosolvent system 10 operationally connected with a superfluid extraction system 100. The superfluid cosolvent system 10 injects cosolvent into a superfluid extraction system 100 at temperatures and pressures compatible with the superfluid extraction system such that the amount of cosolvent can be varied and performed in-line without disrupting the extraction run. The system shown in FIG. 1 uses carbon dioxide as the superfluid or main solvent and $CO_2$ is referred to herein as the main superfluid solvent, however it is clear that other superfluids may be used in a similar system.

On the supply side of the superfluid cosolvent system 10, cosolvent is supplied to the extraction system at compatible temperatures and pressures to the extraction system. The cosolvent system comprises a cosolvent pump 14 which pressurizes and delivers clean cosolvent to the superfluid extraction system 100 from cosolvent supply tank 18, also sometimes referred to as a cosolvent feed tank, through a valve by cosolvent pump 14. Solvent supply tank 18 is preferably connected with a gas supply line to provide the supply tank with an inert gas blanket. Cosolvent pump 14 is a high pressure positive displacement pump and is preferably a pneumatic pump, however can be any other pump compatible with the high pressure systems required for superfluid extraction capable of discharging high pressure solvent at the same or higher pressure than the superfluid process stream. Some examples of high pressure pumps include but are not limited to electrically, hydraulically, or pneumatically driven pumps. Preferably, the high pressure cosolvent pump 14 can increase solvent pressure to at least 10,000 psi, which is sometimes desirable for the superfluid extraction system. Once supplied to the superfluid extraction system, the cosolvent and superfluid are mixed in a superfluid cosolvent mixer 116, which directs the mixture to an extraction column 110 in the extraction system. A valve assembly directs the flow of the cosolvent from the cosolvent pump 14 into the extraction system 100, or alternatively cosolvent can be direct along fluid lines or in a loop to purge the cosolvent process lines, or expose other process lines to cosolvent for cleaning.

The cosolvent system 10 can comprise one or more cosolvent tanks which each comprise one or more cosolvents or cosolvent mixtures according to the process requirements, and each of the solvent tanks can have its own valve assembly connected to the cosolvent control system 20 to control the amounts of the one or more solvents or solvent mixtures into the superfluid extraction system, providing a variety of possible solvent-cosolvent mixtures at which the extraction process can be run. Each solvent tank can also be connected to its own cosolvent pump or to a single cosolvent pump via a valve assembly. The cosolvent pump 14 draws clean cosolvent from the one or more cosolvent supply tanks and injects the cosolvent at a controlled rate through a valve manifold, preferably just before one or more heat exchangers in the superfluid extraction system, via high pressure cosolvent supply line 118 into the superfluid extraction system 100. Cosolvent flow rate can be moderated with pneumatic proportional control valve on the pneumatic vent line of the cosolvent pump 14, and preferably with either or both of feedback from a flowmeter on the suction side of the cosolvent pump 14, such as a laser reading total pump stroke or other flow monitor device. $CO_2$ pump status and $CO_2$ flow through the extraction system can also be used as inputs from the extraction system to the cosolvent system to further integrate the two systems.

In the superfluid extraction system 100 a separator, shown here as a cyclone separator 114, and a liquid to gas vapor separator 106 collect liquid cosolvent and desired extractants from the extraction column 110. The extraction system can have one or more separator(s), of the same or different type, depending on the desired process requirements, the output of each separator being directed to the collection vessel 16. One or more valve assemblies in the extraction system directs the flow of cosolvent and extractant and potentially superfluid $CO_2$ from the one or more cyclones and/or separators to the collection vessel 16. Superfluid management system 112 maintains the main superfluid extraction solvent in its superfluid state, which requires a combination of temperature and pressure control devices and systems. In particular, the superfluid management system 112 comprises one or more high pressure pumps, heat exchangers, heating/cooling jackets, superfluid recyclers, condensers, and other equipment to enable maintenance of the superfluid at the desired liquid/gas conditions at the desired locations in the system. Superfluid management system 112 further comprises a control system to control all of the superfluid control components to monitor and adjust the temperature and pressure of fluid in the extraction system. The cosolvent control system controls the valves and process lines that integrate the superfluid cosolvent system with the $CO_2$ extraction machine. An integrated cosolvent human machine interface (HMI) can allow an operator to control the system injection, drain, and alarm parameters.

Once the superfluid solvent and cosolvent mixture have gone through the extraction system, the extractant and solvent-cosolvent mixture is directed through a high pressure extract transfer line 120 from cyclone separator 114 and gas/liquid separator 106 to collection vessel 16 in the superfluid cosolvent system 10. The collection vessel 16 receives the mixture of superfluid solvent, cosolvent, and extractant and is isolated at an inlet valve and outlet valve, whereupon the collection vessel is depressurized. The collection vessel 16 can receive high pressure liquid, superfluid, cosolvent, solids, extractants, dry ice, liquid $CO_2$, $CO_2$ vapor, and mixtures thereof. The collection vessel 16 has a pressure release control valve and is vented to a hazardous vapor vent system to control the depressurization and the evacuation of vaporizable and gaseous components of the collected mixture during the depressurization. When the collection vessel 16 is depressurized to atmospheric pressure after a high pressure collection cycle, any vapour or gaseous substances can be further directed out of the collection vessel 16 through collection vessel outlet 32 which is optionally assisted by vent fan 22. Upon depressurization the superfluid is vented off and either collected for recycling or vented, optionally assisted using vent fan 22. Any vaporized or gaseous cosolvent can also be reclaimed in a condensation process or vented. The remaining cosolvent and extractant from the superfluid extraction system remaining in the collection vessel 16 can then be directed into an extract transfer tank 24. The collected extract can then be removed for additional processing, which may include one or more additional purification steps, chromatography, and/or cosolvent removal.

The piping system connecting the components of the cosolvent system and extraction system are high pressure lines sufficient to safely contain high pressure cosolvent and liquid or supercritical fluid, such as supercritical $CO_2$. Preferably all the piping and instruments are insulated to protect the components and reduce heat exchange with the environment. The piping system on the cosolvent supply side where the clean cosolvent is drawn for injection into the extraction system is completely closed and isolated from the extract transfer line where the spent cosolvent, extractant, and superfluid collection occurs. The piping system is also preferably static dissipating, meaning that static electricity is reduced by allowing electric charges to flow more slowly through the material for greater control. Reducing static in the system protects electrostatic-sensitive devices, such as electronic valves and control devices in the control system and protects the system in the case of accidental release of flammable liquids or gases. This is particularly important when flammable cosolvents are used, such as methanol or ethanol. The present superfluid system is designed to be fully sealed during operation and opening a vessel or fitting while under pressure will result in the rapid release of gas and the material contained inside the vessel or piping.

The cosolvent system 10 periodically collects the oil and cosolvent mixture, also called the extractant, from the separators in the extraction system 100 throughout the run by opening automated valves and allowing the product to flow into the collection vessel 16. This collection sequence is based on the injected volume into the system and the valves will open to ensure the volume in the cyclones stays below an acceptable level. The oil and solvent mixture is collected from the collection vessel 16 and this can be done during or after the injection. An automated interlock valve can be present on the collection valve intake or between the one or more separator(s) and the collection vessel 16 to prevent the collection vessel from being drained while under pressure, and the interlock safety valve can be configured to close if the separator drain valves open if the system is not pressurized.

Cosolvent control system 20 controls the one or more pumps, valves, and flow lines to control the amount, type, and flow rate of cosolvent into and out of different components of the cosolvent system 10. The control system can comprise one or more control panels, microcontrollers, solenoids, valves, flow restrictors, temperature and pressure control components, drivers, air flow components, regulators, chemical sensors (such as chromatography devices and other chemical sensing devices), physical sensors (such as for temperature, pressure, air flow, and fluid flow), communication and data lines, connection ports, control panel connection banks, and the electrical and/or communication connections therebetween. Control system communication lines 36 connected to the controllable valves, pumps, and other components of the cosolvent system 10 control the operation of each component to achieve the desired process controls. A plurality of valve assemblies in the piping system control fluid flow to and from components to provide the process control, and the valve assemblies are controlled by the cosolvent control system 20, an extraction system control system, or other control system. The cosolvent control system 20 regulates the discharge flow and pressure of the cosolvent pump 14, which provides a steady or variable cosolvent concentration to the extraction column as desired during the process. The control system can also automatically drain cosolvent and extract from the extraction machine and transfer the pressurized fluid from the one or more extraction cyclones and/or separators into the cosolvent collection vessel 16. To do this, the control system actuates one or more valve assemblies for timed-interval draining or volume-interval draining of cosolvent and extracts from the one or more cyclone collectors or gas/liquid separators, or other components in the extraction system.

The cosolvent control system 20 can also provide instructions to one or more of the plurality of valve assemblies in the cosolvent system 10 to inject one or more cosolvents in an isocratic, step, or linear regime according to the process recipe. The control system can also store recipes generated by the user based on input material. The control system regulates cosolvent injection rate, which can be between 0.01% and 99% by mass of the $CO_2$ flow rate, and is preferably between 0.1-10% by mass in liquid or superfluid carbon dioxide. The control system can be configured for multiple cosolvent densities such that the cosolvent system can control the flow rate of the cosolvent by identifying the physical properties of the cosolvent and adjusting the process parameters accordingly. The control system also provides safeguards to prevent the draining of the collection vessel while it is pressurized. The cosolvent control system 20 can also limit the injection of cosolvent into the $CO_2$ extraction system if the safe volume of dissolved cosolvent in the extraction machine is approaching a hazardous limit. The control system will also limit the injection of cosolvent if safe operating parameters on the superfluid extraction machine are not met. The control system has safety controls in place for emergency shutdown scenarios of both systems. The cosolvent system can also comprise one or more sensor for determination of the cosolvent residual in the superfluid exiting the extraction column to provide an indication of the cosolvent amount in the extracted biomass. This is useful as solvent contaminated biomass requires special handling, and biomass with low solvent residual can be treated as non-hazardous waste, such as a cosolvent residual of less than about 5000 ppm. A similar or different sensor can also be used to detect the residual concentration of cannabinoids or other extracted oils from the biomass to determine when the extraction is complete. This is useful to determine when the extraction is complete so as not to extract undesired compounds. This can also reduce overall extraction time and process cost. A temperature sensor in the extraction column 110 monitors the temperature of the biomass and is particularly important for ensuring complete cryofreezing of the biomass in a preliminary cooling step prior to extraction.

The cosolvent system can also function as a clean in place system for a superfluid extraction machine to clean an extraction column, cyclone separators, and liquid-gas separators, and other components of a superfluid extraction system by exposing interior surfaces with solvent to dissolve contaminants. This is particularly useful in difficult-to-reach areas of an extraction system and can assist in cleaning without requiring deconstruction or disassembly of the extraction system. The presently described cosolvent system is designed to use a class 3 solvent as defined by the FDA, which are acetic acid, acetone, anisole, 1-butanol, 2-butanol, butyl acetate, tertbutyl methyl ether, dimethyl sulfoxide, ethanol, ethyl acetate, ethyl ether, ethyl formate, formic acid, n-heptane, isobutyl acetate, isopropyl acetate, methyl acetate, 3-methyl-1-butanol, methyl ethyl ketone, 2-methyl-1-propanol, pentane, 1-pentanol, 1-propanol, 2-propanol, propyl acetate, and triethylamine. However other cosolvents may be used under strict conditions and with appropriate removal procedures from any product destined as a human or animal consumable. Other potential cosolvents include gases hydrogen, neon, nitrogen, and argon; hydrocarbons such as methane, ethane, toluene, propane, butanes, pentanes, and hexanes; halogenated hydrocarbons; ammonia; and organic solvents such as methanol, 1-hexanol, 2-methoxy ethanol, tetrahydrofuran, 1,4-dioxane, acetonitrile, methylene chloride, dichloroethane, chloroform, propylene carbonate, N,N-dimethylacetamide, and carbon disulfide. One or more secondary processing units can also be fluidly connected to the cosolvent system by way of the collection vessel 16 outlet or valve connected thereto. The secondary processing units can be used, for example, for dewaxing or winterizing the extractant, for removing solvent or other aromatic compounds, for filtration, or for other processing to obtain the product(s) of interest.

Figure 2:
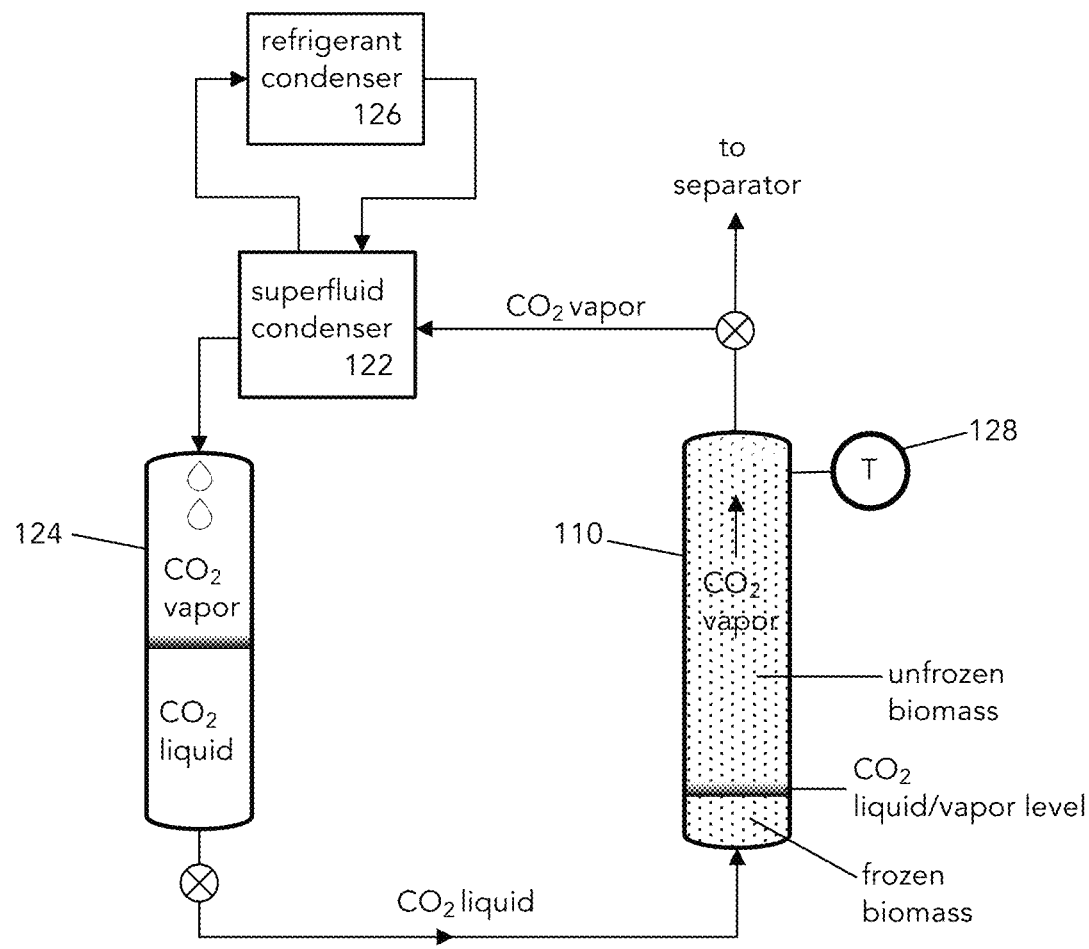
FIG. 2 is a diagram of a refrigerant loop for cryogenic pre-freezing biomass in an extraction column before a liquid carbon dioxide extraction cycle.

FIG. 2 is a diagram of a refrigerant loop for a freezing biomass in a liquid carbon dioxide extraction column before an extraction cycle. To prepare for an extraction, biomass is packed into an extraction column 110. It has been found that cryo-freezing or pre-cooling of the biomass at a temperature of less than 0° C. prior to starting an extraction results in higher purity extracted fractions and better separation of hydrophobic and hydrophilic components from a biomass, particularly when used in combination with a cosolvent/superfluid extraction step. Carbon dioxide is shown as a preferred example of a superfluid in this system, however it is understood that other superfluids may be used.

In a refrigeration loop during a pre-cooling step, liquid $CO_2$ is pumped or directed into the bottom of an extraction column 110 comprising biomass from superfluid accumulator 124. During the preparatory pre-extraction step of cryofreezing or cooling of the biomass, heat from the biomass is transferred to the liquid $CO_2$ which causes boiling, resulting in evaporative cooling and vaporizes the $CO_2$ in the extraction column 110. The extraction column 110 is controlled at a pressure where the saturation temperature of the liquid carbon dioxide is below 0° C. Optimally, the $CO_2$ receiver is temperature controlled and the pressure of the system correlates with a saturation temperature of liquid in the receiver below $-20°$ C. $CO_2$ vapor rises to the top of the column and is recycled in a superfluid condenser 122 which cools the $CO_2$ vapor below the saturation temperature back to liquid form and directs it into the superfluid accumulator 124 for recirculation. Refrigerant condenser 126 removes heat from the carbon dioxide and exhausts the heat from the refrigeration cycle to the atmosphere. Optimally, waste heat from the refrigeration cycle is used as part of the extraction process for boiling solvents or process control where heat is required. The refrigerant can be $CO_2$ or any other refrigerant capable of removing heat from the circulating solvent $CO_2$. As the biomass in the extraction column 110 freezes the $CO_2$ liquid/vapor level rises, where biomass is frozen below the liquid/vapor level. Once the biomass is frozen the temperature probe 128 at the top of extraction column 110 drops sharply to near the condensation temperature of $CO_2$ at the cryo-freezing temperature of the refrigerant loop indicating that the biomass in the extraction column 110 is frozen. It has been found that by freezing the biomass in a relatively low pressure environment prior to extraction high moisture content biomass can be efficiently extracted without pre-processing. The pressure required for freezing the biomass at 0° C. with liquid $CO_2$ (see $CO_2$ saturation curve in FIG. 18) is about 500 psi, and about 400 psi if the cryofreezing temperature is $-10°$ C., while maintaining the $CO_2$ in liquid state.

Pressure of the superfluid accumulator 124 is generally controlled by controlling the refrigeration system to maintain the vapor/liquid temperatures at the desired saturation point. It is understood that with additional heat exchangers before extraction column 110 for cooling the superfluid at the inlet, or one or more compressors at the discharge of extraction column 110 to reduce the column pressure and thus fluid saturation temperature, the extraction column 110 and the accumulator 124 can exist at different temperatures and pressures. Optimally the system is configured so that the pressure drop between the top of extraction column 110 and accumulator 124 is minimal, or isobaric. With both vessels accumulator 124 and extraction column 110 operating near same saturation properties, high mass flow rates are achievable with a near saturated vapor leaving extraction column 110 and entering accumulator 124, reducing the time required for freezing the biomass.

Figure 3:
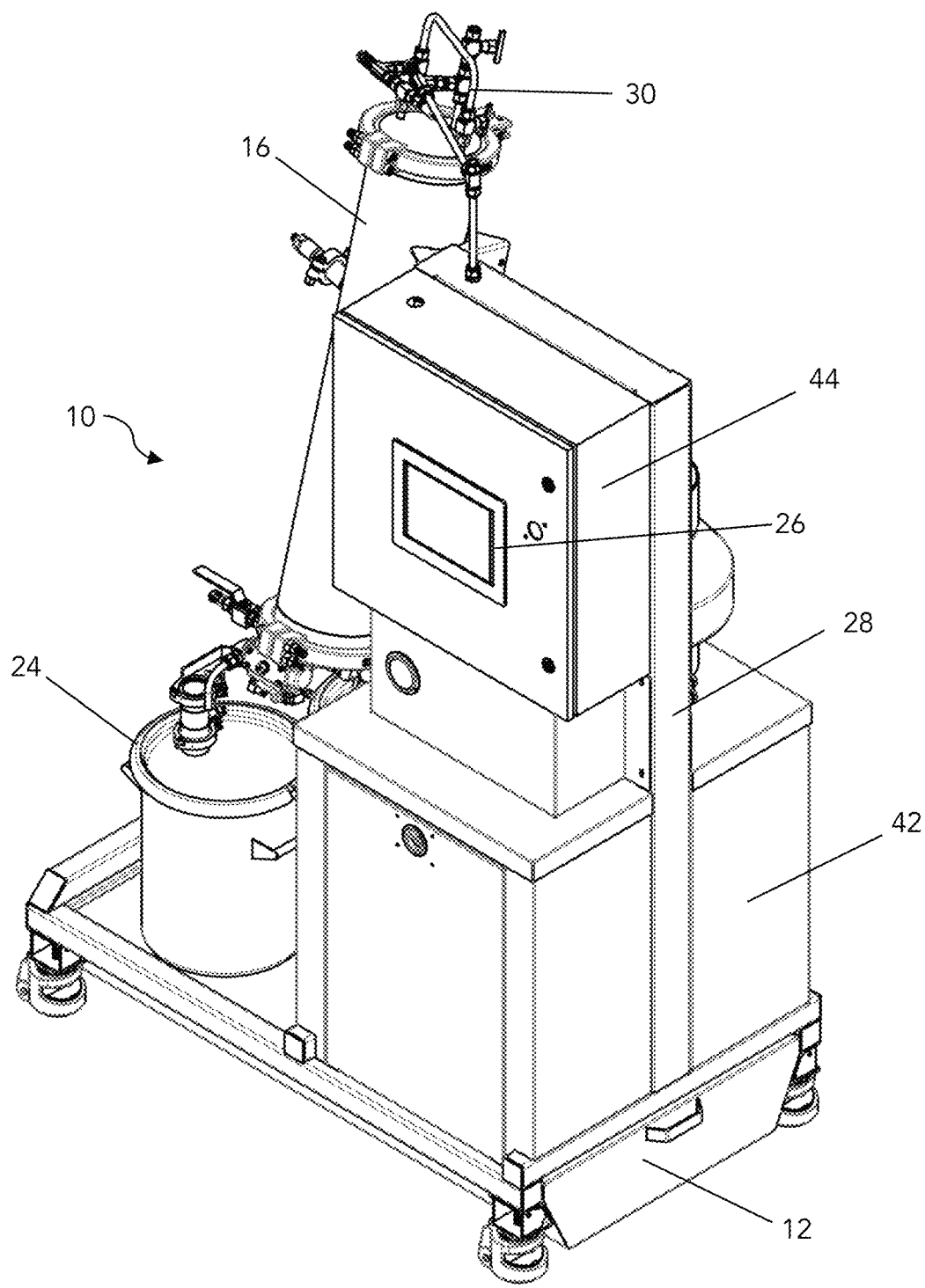
FIG. 3 is a front isometric view of a cosolvent supply system.

FIG. 3 is a front isometric view of an embodiment of a superfluid cosolvent system 10 on a support base 12. The support base 12 can be a flat base, but can also preferably serve as a spill containment system which is a safety feature required when working with solvents. In particular, support base can server as a spill containment tray to catch leaks or spills of cosolvent from the extractant collection and pump area of the cosolvent system. Support base 12 can also comprise a riser structure to lift the support base off the ground to provide mobility and/or air flow under the cosolvent system 10. In this way the support base 12 can serve as a solvent spill reservoir which can hold a greater volume of solvent than the one or more cosolvent supply tank, extract transfer tanks, or combination thereof. The collection vessel 16 which collects cosolvent from the extraction system is preferably structurally supported by a structural frame, and the support base 12 can also optionally be integrated into structural support frame 28. Structural support frame 28 holds the collection vessel 16 in place and supports and secures the other components of the cosolvent system 10. Collection vessel intake 30 at the intake of collection vessel 16 receives a mixture of extractant, solvent, and cosolvent at high pressure, through at least one valve or valve manifold controlled by the cosolvent control system and or extraction system.

One or more extract transfer tank 24 is connected to the outlet of collection vessel 16 to receive a mixture of depressurized cosolvent and extractant. The outlet of the collection vessel 16 is designed such that the extract transfer tank 24 can be easily removed and swapped out for a clean extract transfer tank 24 to enable separation of fractions coming from the extraction system. The outlet of the collection vessel 16 can also be fitted with a valve manifold to direct the collected extractant into a desired fluid line for collection. An output for the cosolvent control system can be displayed on display screen 26, and some or all of the control hardware for the cosolvent control system can be housed and protected in control system enclosure 44. The display screen 26 can provide a human-machine interaction site on the cosolvent system to provide an indication of the set preferences, system status, and optional input control of the cosolvent system. The system display screen can provide an interactive port for access and reporting from the control system to a human technician, and the same data can also potentially be sent to one or more peripheral or external computers, computing devices, or electronic components. The system control screen can provide process information on the process progress, time to completion, as well as process recipes and associated process and equipment parameters. Actions can also be initiated by a technician from the control screen, such as draining specific equipment, valve control, drain sequences, solvent and superfluid recovery protocols, and drain protocols. Alarms and reminders can also be displayed and the system can confirm that certain technician checks have been done through the human machine interface. The control system, via the control screen on the cosolvent system or other device, can also provide information on the rates of superfluid flow and supply, cosolvent flow and supply, and run information. Data from the control system can also be collected and sent to one or more computing device for additional analysis, recording, or storage.

Pump enclosure 42 contains and protects the cosolvent pump and other mechanical components. The cosolvent pump is fluidly connected to one or more cosolvent supply tanks and to the extraction system via one or more valve manifolds. Preferably, pump enclosure 42 is integrated with the support frame 28 is ventilated to the exterior to exhaust any hazardous vapors, such as from the cosolvent. The power for the cosolvent system is preferably interlocked with the ventilation system and the module must only be able to be powered on if the ventilation system is running. Regulations require minimum volumes of air flow in areas where solvent is used, and coupling the ventilation with the cosolvent system ensures that when solvent is flowing an appropriate and safe level of ventilation is provided around the cosolvent system. This can be accomplished by electrically coupling the power for the ventilation system and the power for the control panel.

Figure 4:
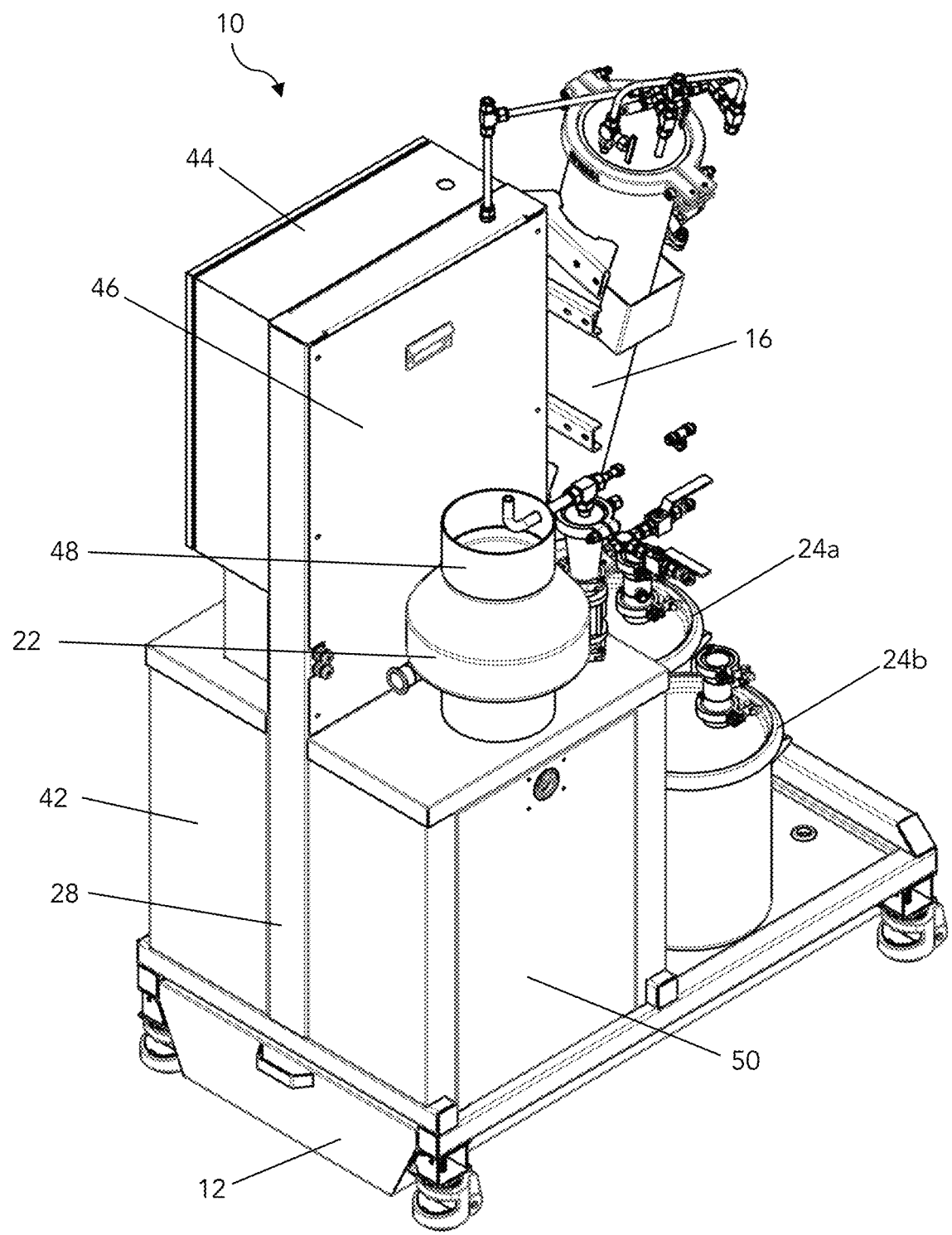
FIG. 4 is a rear isometric view of a cosolvent supply system.

FIG. 4 is a rear isometric view of a cosolvent system 10 showing support base 12, support frame 28, collection vessel 16, and extract transfer tanks 24a, 24b. Control system panel 46 can be opened to provide access to control system enclosure 44 which comprises electrical and electronic hardware components to operate the cosolvent control system. Pump enclosure door 50 provides access to the pump enclosure 42 which houses the cosolvent pump and other fluidic and mechanical components of the system. The housing system shown for the mechanical and electrical components is optional, and can be configured in a variety of different ways, such as, for example, side-by-side, stacked, integrated or not with a structural frame, or with other components in the housing, as well as integrated into the superfluid extraction system. Optional vent fan 22 and air flow duct 48 provide air flow to the pump enclosure to evacuate any leaked solvent to comply with solvent storage and handling regulations.

Figure 5A:
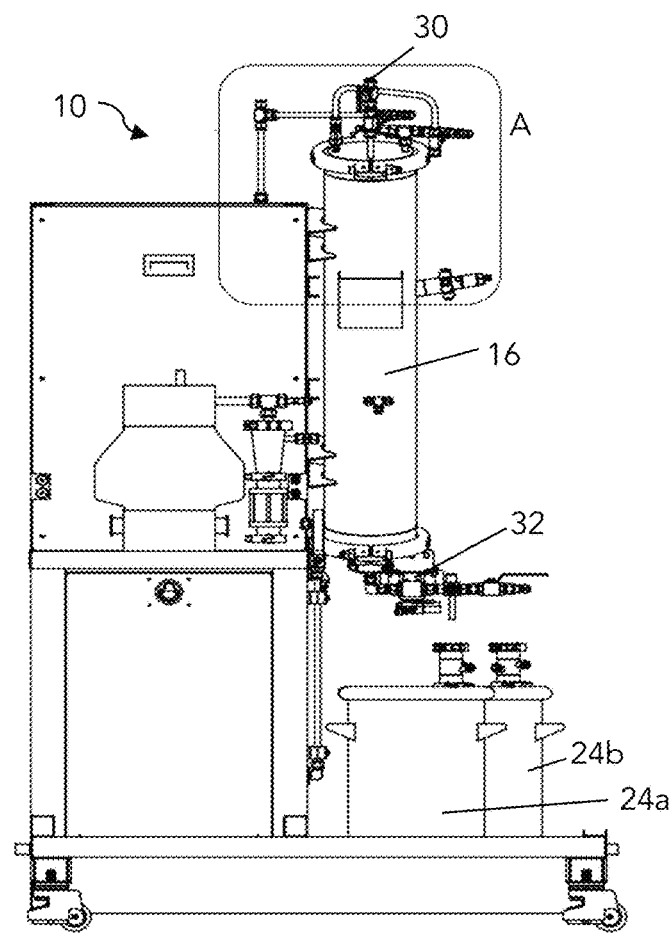
FIG. 5A is a rear view of a cosolvent supply system with collection vessel intake.

FIG. 5A is a rear view of a superfluid cosolvent system 10 with collection vessel intake 30. The collection vessel 16 connects with a separator in the extraction system at collection vessel intake 30. Extract transfer tanks 24a and 24b are positioned at the collection vessel outlet 32 to receive the outflow from collection vessel 16 comprising extractant and optionally also one or more cosolvent and the collection of multiple desired fractions. More than two collection vessel tanks can optionally be connected based on the system and extraction requirements.

Figure 5B:
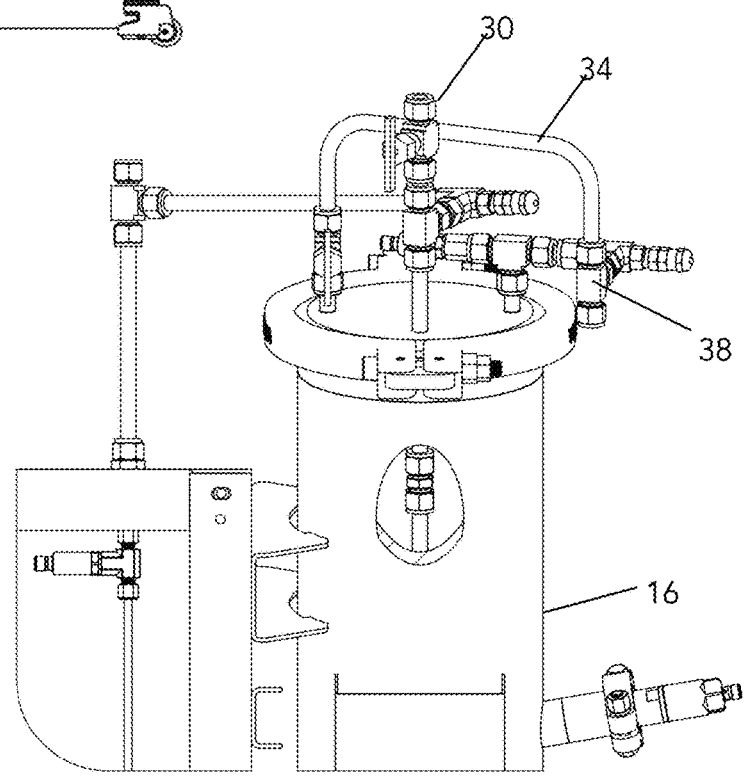
FIG. 5B is a closeup view of a collection vessel intake system at detail A shown in FIG. 5A.

FIG. 5B is a closeup view of a collection vessel intake system at detail A shown in FIG. 5A. Collection vessel intake 30 is a high pressure transfer line that receives a mixture of superfluid, extractant, and optionally one or more cosolvent, to the collection vessel 16. The collection vessel receives and collects cosolvent and extractant oil from the superfluid extraction system as discharge from one or more superfluid separators. Although the present system is designed to safely accommodate cosolvent, it is understood that the collection vessel may also be used to collect mixtures of superfluid and extractant from an extraction system in the absence of cosolvent. In the transfer of fluid from the extraction system to the collection vessel 16, it is preferable that fluid is directed downward and in a tangential direction toward the inner side wall of the collection vessel to prevent spray and to have more control over the fluid transfer. Vapor discharge line 34 provides a vent to the collection vessel to reduce pressure in the vessel, and pressure relief valve 38 connected to vapor discharge line 34 discharges vapor and gas out of the collection vessel 16 and into a liquid trap. At the liquid trap vaporized solvent is recovered and desolvated gas is directed out of the system through exhaust vent lines.

Figure 6:
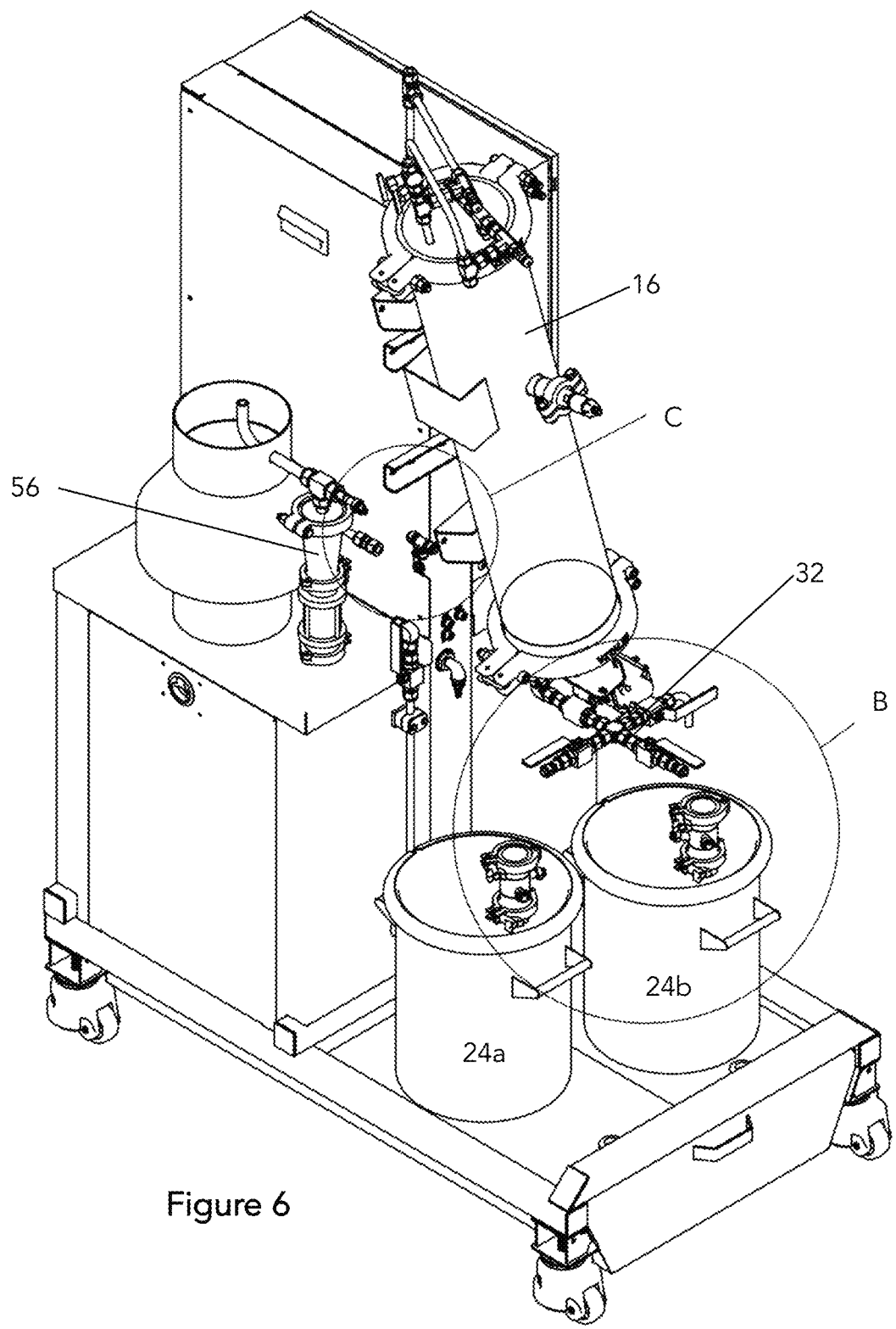
FIG. 6 is an isometric view of a cosolvent supply system with collection vessel and extract transfer tanks.

FIG. 6 is an isometric view of a cosolvent system with collection vessel 16 and extract transfer tanks. Extract transfer tanks 24a and 24b are positioned at the collection vessel outlet 32, which can have one or more valves to connect the collection vessel 16 to the extract transfer tank to transfer collected depressurized extract and cosolvent mixture. The collection vessel 16 can transfer the mixture out through the collection vessel outlet by gravity, or using a liquid transfer assist such as a pump or differential pressure or vacuum. Vaporized solvent and pressurized gas can also be shunted to liquid trap 56 during extractant collection to collect any vaporized solvent. Shown are two 25 L extract transfer tanks 24a, 24b used to transfer product from the cosolvent system to post processing, however the tanks can be of any desired size. As the present system is intended for large scale multi-litre extractions, the extract transfer tanks should be of a reasonable volume to contain the collected extractant from the collection vessel. The extract transfer tanks 24a and 24b can also be easily swapped out and as the extractant solution released from the collection vessel 16 is not pressurized, the transfer tanks must be solvent safe, but do not have to be high pressure containers. Optionally lines from the collection vessel valve assembly at the collection vessel outlet 32 can be routed into another room where secondary processing is done. Optionally one or multiple valves are connected to an in-line winterization device which removes fats and waxes from the extractant.

Figure 7A:
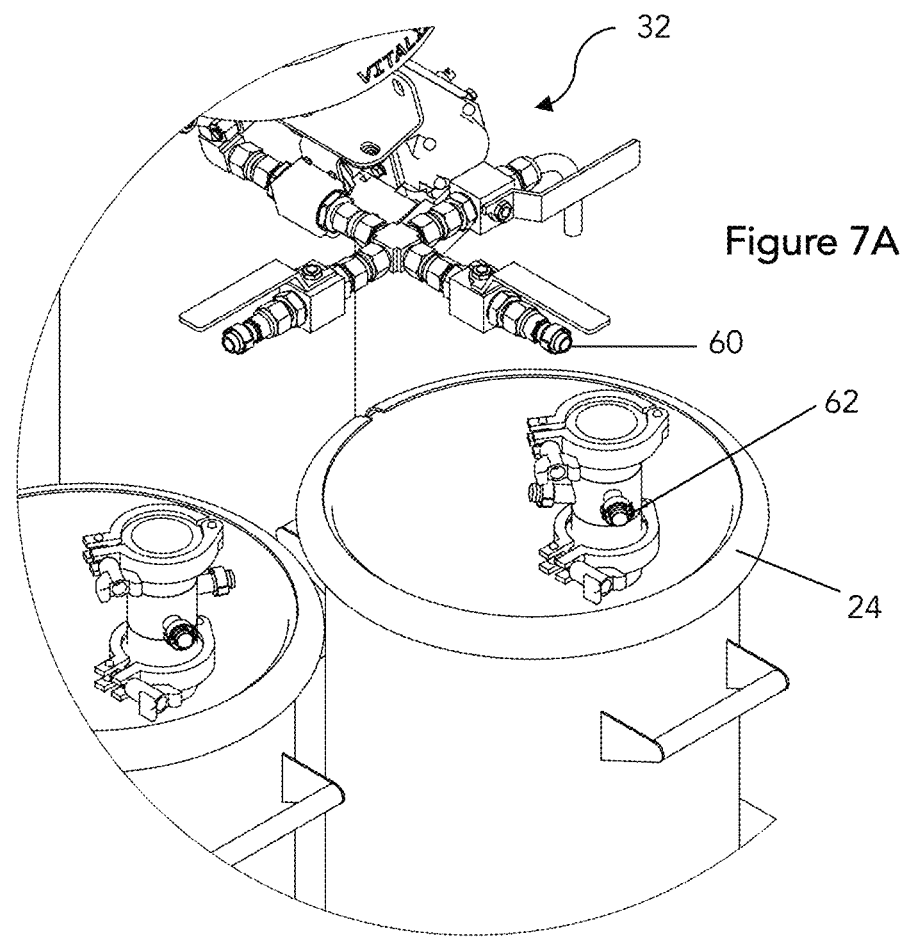
FIG. 7A is a closeup isometric view of the collection vessel outlet system and extract transfer tanks at detail B in FIG. 6.

FIG. 7A is a closeup isometric view of the collection vessel outlet system and extract transfer tanks at detail B in FIG. 6. Collection vessel outlet 32 shown has a valve assembly with three outlet valves that can be connected with piping or tubing to extract tank 24. The valve assembly can also comprise a valve bank having one or more extract outflow valve 60, which can be manually controlled or automatically actuated by the control system to open such that extractant fluid can be collected from the collection vessel. Each valve can also have one or more manual sampling valves to enable sampling of outflow from the collection vessel prior to bulk collection in an extract transfer tank. Each extract transfer tank 24 can also be fitted with a vapor/gas outlet 62 to collect any solvent vapor and direct the vapor/gas through an exhaust vent line to a liquid trap to collect vaporized solvent and exhaust any remaining gas.

Figure 7B:
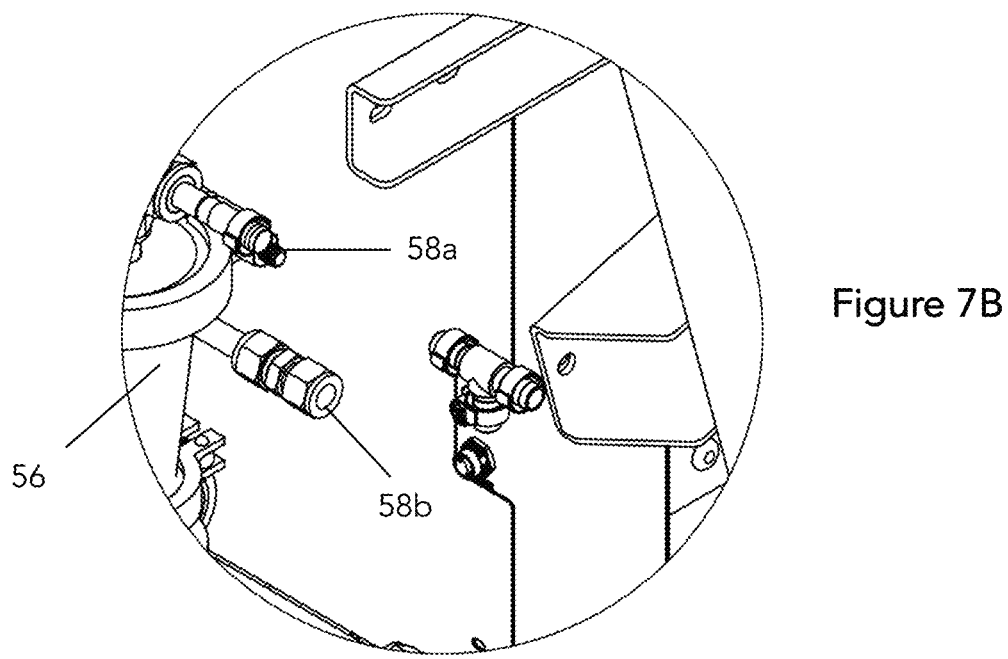
FIG. 7B is a closeup isometric view of the liquid trap at detail C in FIG. 6.

FIG. 7B is a closeup isometric view of the liquid trap at detail C in FIG. 6. During extractant and cosolvent collection the mixture of collected superfluid, cosolvent, and extractants are transferred to the collection vessel and depressurized in the collection vessel to enable removal and recycling of superfluid and collection of the extractant-solvent mixture at ambient temperature. Pressure reduction from superfluid pressure to ambient is extreme, and exhaust vent lines connect components such that pressure can be released in the system. Vaporized solvent and pressurized gas released during extractant collection is shunted through exhaust vent lines 58a, 58b to liquid trap 56 to collect any vaporized solvent.

Figure 8:
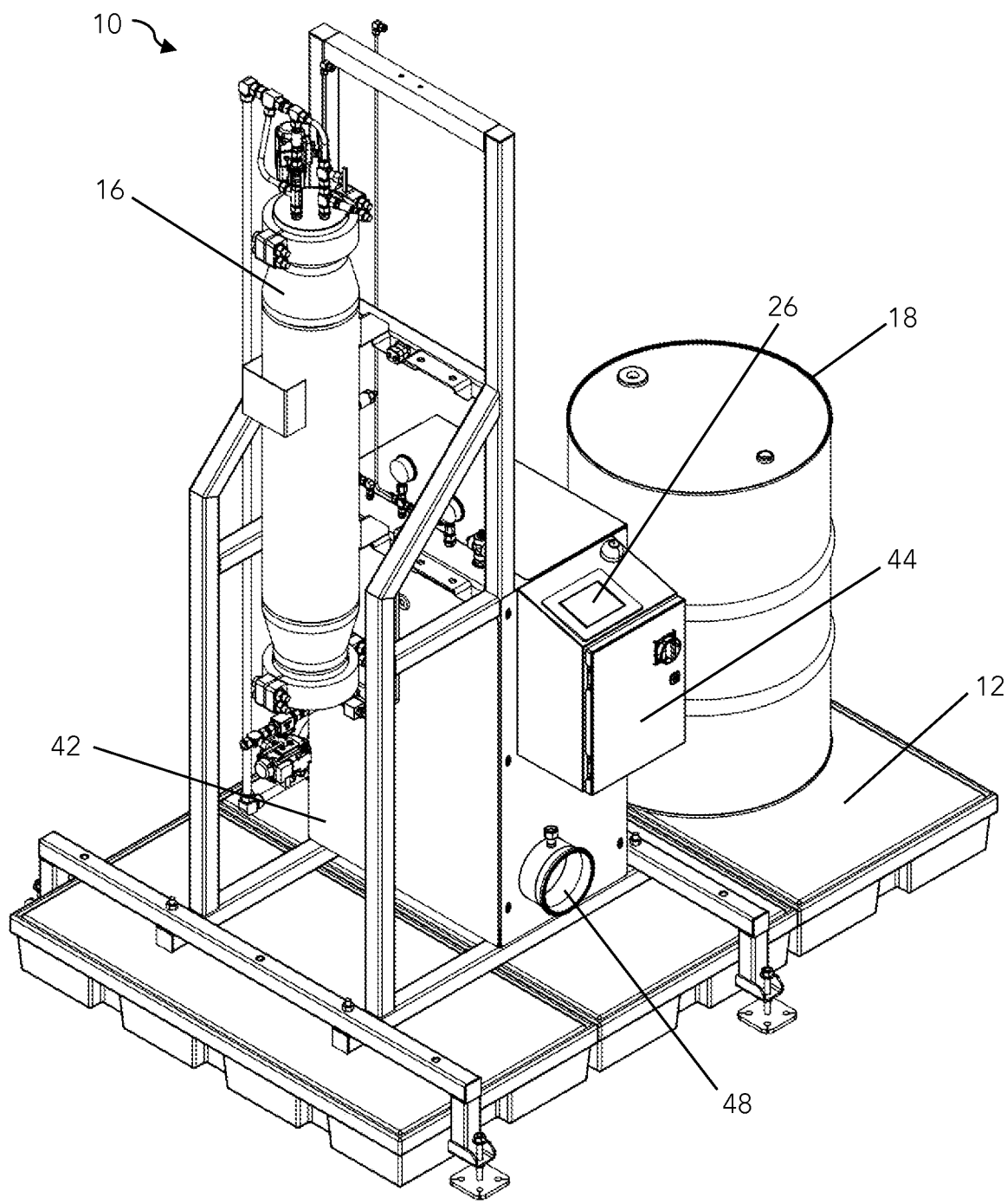
FIG. 8 is an isometric view of another example cosolvent system.

FIG. 8 is an isometric view of another example cosolvent system 10. In this embodiment the cosolvent supply tank 18 is on the support base and does not require a secondary containment tank. Instead a support base 12 is provided for the cosolvent supply tank, and the support base 12 supports the cosolvent supply tank and secondary containment tank is integrated with the support base 12 for the cosolvent system 10. Cosolvent control system is housed in a control system enclosure 44 and a display screen 26 on the enclosure provides status information and/or manual control of the cosolvent system. Pump enclosure 42 is also shown with air flow duct 48 on the side of the pump enclosure 42 to collect any vaporized cosolvent.

Figure 9A:
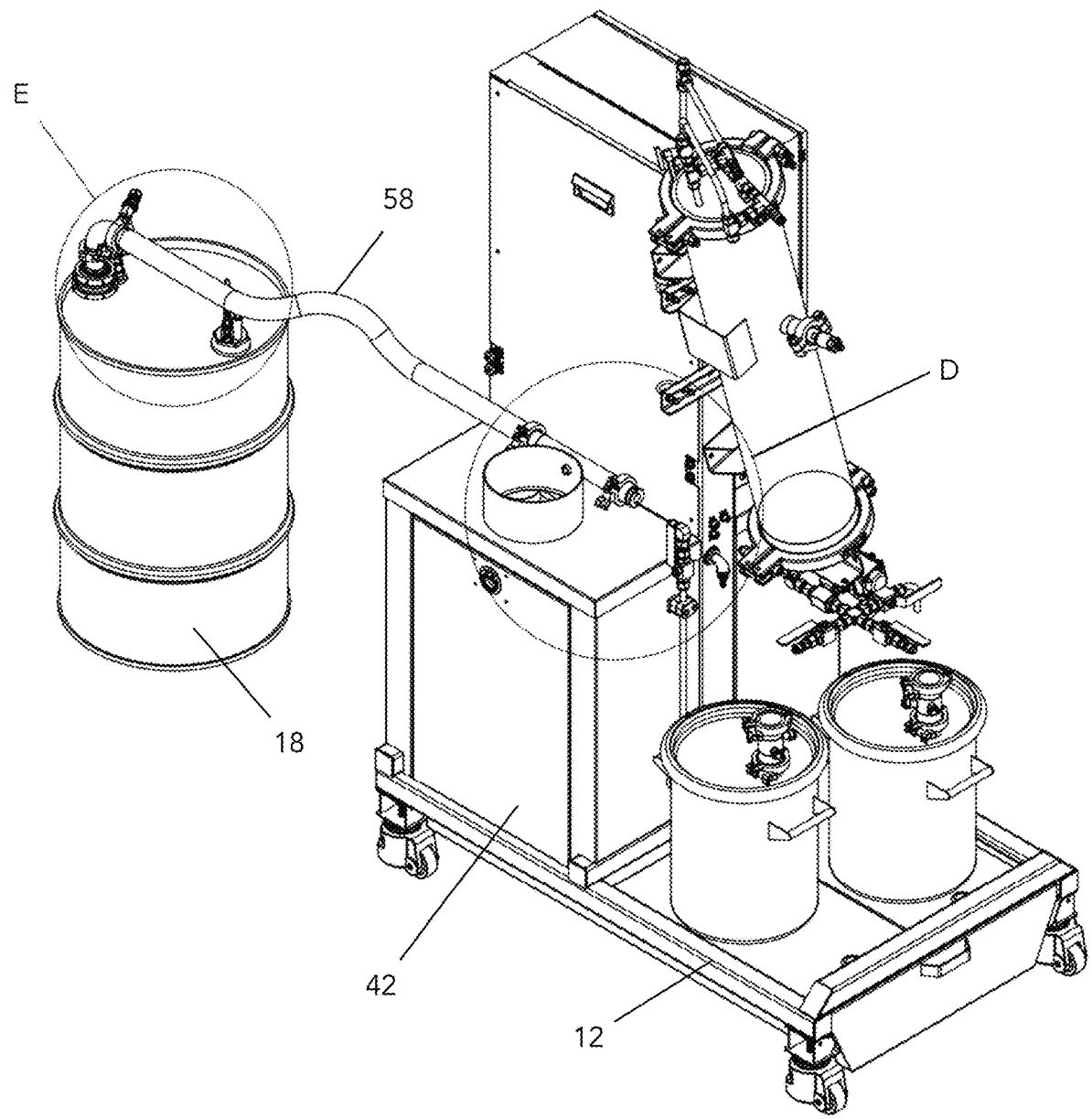
FIG. 9A is an isometric view of a cosolvent supply system with solvent feed tank in a secondary containment tank.

FIG. 9A is an isometric view of a cosolvent system with solvent tank in a secondary containment on a support base 12. The cosolvent supply tank 18 is housed inside a secondary containment tank which is hidden in this view for clarity, and secondary containment tank and cosolvent supply tank 18 are vented to the pump enclosure 42 through exhaust vent line 58 to capture any solvent that may have vaporized from the cosolvent tank. The solvent tank can be a stationary tank which stores and supplies clean solvent to the cosolvent pump, or can alternatively be a mobile tank which used to transport clean ethanol to and from the cosolvent system. The cosolvent supply tank has a drip free push connect fitting which can be connected to a moveable and/or portable filling tank for closed transfer when the supply tank is empty.

FIG. 9B is a close-up view of vent detail D in FIG. 9A. Pump enclosure is connected to exhaust vent line 48. In one embodiment, a solvent supply line from the solvent supply tank inside the secondary containment tank can run concurrent and inside the exhaust vent line 58 such that forced air flow around the solvent tank inside the containment vessel, sealed off to the outside, is directed to a vent system and does not escape the containment system. Any solvent vapor that may have escaped either into the secondary containment tank or from the solvent transfer lines can thus be shunted through the exhaust vent line 58 and into the pump enclosure 42. Air flow duct 48 is connected to a means for evacuating air from the pump enclosure, such as one or more vacuum pumps or vent fans or a combination thereof, and solvent is thus safely contained within the cosolvent system. The evacuation means and closed vent lines provides a safety feature which is integrated into pump module and operates when cosolvent is present in the room where the cosolvent system resides. The vent system is also preferably connected to the liquid trap which collects droplets from the vent lines to prevent carryover into the ducting and ventilation system.

FIG. 9C is a close-up view of the top of the feed tank shown as detail E in FIG. 9A. Connect fitting 68 is a leak free push connect fitting used for closed transfer of cosolvent from a mobile solvent supply tank into the feed tank. Shutoff valve 70 can stop cosolvent flow from the supply tank to the cosolvent pump and is connected to a drop tube which draws clean cosolvent from the cosolvent supply tank. Solvent valve manifold 72 has two main valves: one valve is connected to the inert gas blanket which provides head pressure to the cosolvent supply tank and helps push cosolvent to the pump while also displacing oxygen and creating an inert environment; and the second valve allows for the release of inert gas within the secondary tank during the filling process. This allows for the safe transfer of cosolvent into the supply tank from another source. The solvent container can also have a fitting or float device which rises when the cosolvent supply tank is full. This visual or electronic indication allows for an operator to stop filling the supply tank when the float 'lifts'. Optionally and preferably the solvent level detection in the cosolvent tank is automated and electronically controlled with suitable components in the control system.

FIG. 9D is a side cross sectional view of the secondary containment tank 40 and cosolvent supply tank 18, which can also be referred to as a feed tank assembly. Solvent supply line 64, which can be a pump suction line, draws solvent from the cosolvent supply tank 18 through drop tube 74 into the cosolvent system and exhaust vent line 58 at the top of secondary containment tank 40 which evacuates air from the headspace of the secondary containment tank 40 and into the venting system. One or more solvent tanks can be fluidly connected to the cosolvent system.

Figure 10:
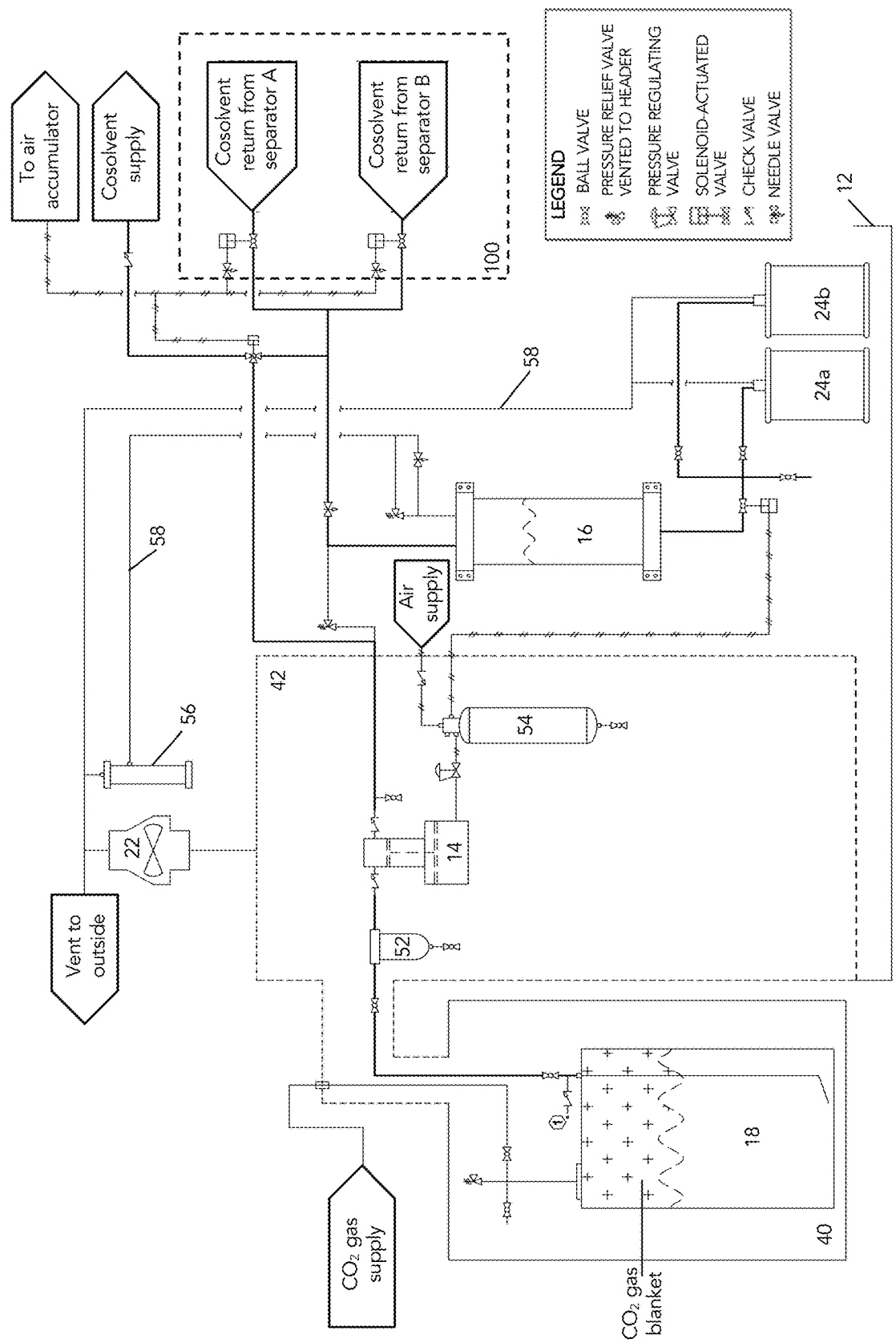
FIG. 10 is a schematic of a superfluid cosolvent system with integration to a superfluid extraction system.

FIG. 10 is a schematic of a superfluid cosolvent system with integration to a superfluid extraction system at the cosolvent supply. In this configuration of the superfluid cosolvent system an inert $CO_2$ gas supply is fluidly connected to a secondary containment tank 40 to provide an inert gas flow and capture any vaporized solvent, and also to the cosolvent supply tank 18 to provide a $CO_2$ gas on top of the solvent level. The secondary containment tank 40 is fluidly connected by exhaust vent lines 58 to evacuate the solvent storage area and direct air through liquid trap 56 and to the outside. Similarly, extract transfer tanks 24a, 24b which also comprise cosolvent when filled can be vented through the exhaust vent lines 58, as well as pump enclosure 42. Support base 12 can support some or all of the components of the superfluid extraction system and can also serve as a secondary containment system to capture any spilled solvent in accordance with solvent handling regulations. Vent fan 22 or other air evacuation means can also direct air away from the cosolvent system and into the exhaust vent lines 58. In this embodiment air is supplied from an air supply to air accumulator vessel 54, and the cosolvent pump is actuated by a pressurised air supply to increase cosolvent fluid to the desired pressure, above the pressure of superfluid, so that the cosolvent can pass through a check valve fluidly connected to the superfluid extractor. Optionally the cosolvent pump can be electric, hydraulic, or use another method for pressurising the cosolvent fluid. In this embodiment the air system also supplies air when required for the actuation of control valves. As a safety feature valves are used where appropriate in a configured state of either 'normally-closed' or 'normally-open' for which that position changes when the air signal is applied. To allow fluid flow through a 'normally-closed' valve the control system can signal an electrical valve to apply air pressure on the actuator of the valve which changes the valve to a 'open' state for fluid to pass through. In the event of electrical loss when the air control valve is open, the air signal to the process valve will drop to no pressure and the 'normally-closed' valve can be mechanically (spring) returned to the closed position, which is desirable when cosolvent needs to be contained. Optionally the process valves can be directly electronically controlled or controlled in other manners to allow, modulate, and prevent flow when required by the control system.

In the system, cosolvent is drawn from one or more cosolvent supply tank 18 through an optional cosolvent filter 52 and into cosolvent pump 14. Although only one cosolvent supply tank is shown, the system can have connections to more than one cosolvent tank holding the same or different cosolvent. The connection of two cosolvent supply tanks of the same cosolvent allows the system to switch to a different cosolvent supply if the first tank is running low; with two or more cosolvent tanks holding different cosolvents or mixtures of cosolvents the cosolvent system can have a wider range of cosolvent extraction methods available and the system can inject different combinations and cosolvents into the extraction system to provide a wider range of cosolvent extraction conditions. From cosolvent pump 14 cosolvent is controllably injected into the cosolvent supply line of the superfluid extraction system and travels from the cosolvent injection location on the $CO_2$ extractor through the extraction chamber to the cyclone separators. Cyclones and secondary separators can purge on a cycle while cosolvent injection continues. In one example when ethanol is used as the cosolvent, 96% of the ethanol is collected in cyclone separators and 4% is collected in secondary separators. A purge cycle can be controlled by a total injected volume setpoint. The cosolvent then drains back to the collection vessel on the cosolvent module. The collection vessels receive the high pressure fluids from the cyclone and regulates the input valve to maintain a desired collection vessel pressure, as the fluids separate in the collection vessel, the gasses are directed out of the collection and it is continuously vented through line 58. When fully depressurized, the control system allows for collection vessel drain valve connected to the collection vessel to be opened, and the extractant oil collected. Preferably, the system can automatically drain ethanol cosolvent and product from the separation series on the extraction system into the collection vessel in the cosolvent system.

The cosolvent system periodically collects the oil and cosolvent mixture from the cyclones throughout the run by opening automated valves and allowing the product to flow into the collection vessel on the pump skid. This collection sequence is based on the injected volume into the system and the valves will open to ensure the volume in the cyclones stays below an acceptable level. The extractant oil and solvent mixture will be collected from the collection vessel and this can be done during or after the injection. Preferably, an automated interlock valve to prevent the vessel from being drained while under pressure. When the superfluid-extractant mixture returns from being processed by the extraction system 100, the liquid/gas mixture is directed through high pressure fluid lines to collection vessel 16, where controlled depressurization of the superfluid occurs and the evaporated $CO_2$ can be separated from the cosolvent-extractant mixture, which is then directed to extract transfer tanks 24a, 24b at ambient or near ambient pressure. Separators A and B are shown as part of the extraction system, however it is understood that the cosolvent system can be connected to one or multiple separators, cyclone separators, gas/liquid separators, or other components of the extraction system, and fluid lines can be controllably opened and closed by multiple fluid valves, optionally with valve assemblies or valve manifolds. Exhaust vent lines 58 are preferably also connected to extract transfer tanks 24a, 24b to relieve any pressure above ambient and direct any gas or vaporized solvent out of the cosolvent system. The system is designed to stop injection automatically after each injection window has been achieved.

After the injection has stopped there will still be solvent in the main $CO_2$ line and extraction chambers. After the cosolvent flow is turned off the extraction system can be run with superfluid only to ensure that the solvent has been flushed out of the extractors through the separators and into the collection vessel 16. When the pump has been stopped the draining of the cosolvent from the system will continue to remove the cosolvent from the extraction vessels and lines. By flushing the extraction system with superfluid only, any remaining cosolvent is washed out of the plant material in the extraction column, which avoid the disposal complications of ethanol soaked biomass. To ensure the ethanol is completely recovered the system volume should be changed out twice. Once the extraction column is fully flushed with $CO_2$ the extraction column can be depressurized and the remaining biomass in the extraction column can be removed and treated as standard organic waste. Removing all of the excess cosolvent enables the biomass waste to be treated normally rather than as chemical-contaminated waste, reducing costs to the processor and reducing the amount of waste consumed by the process.

Figure 11:
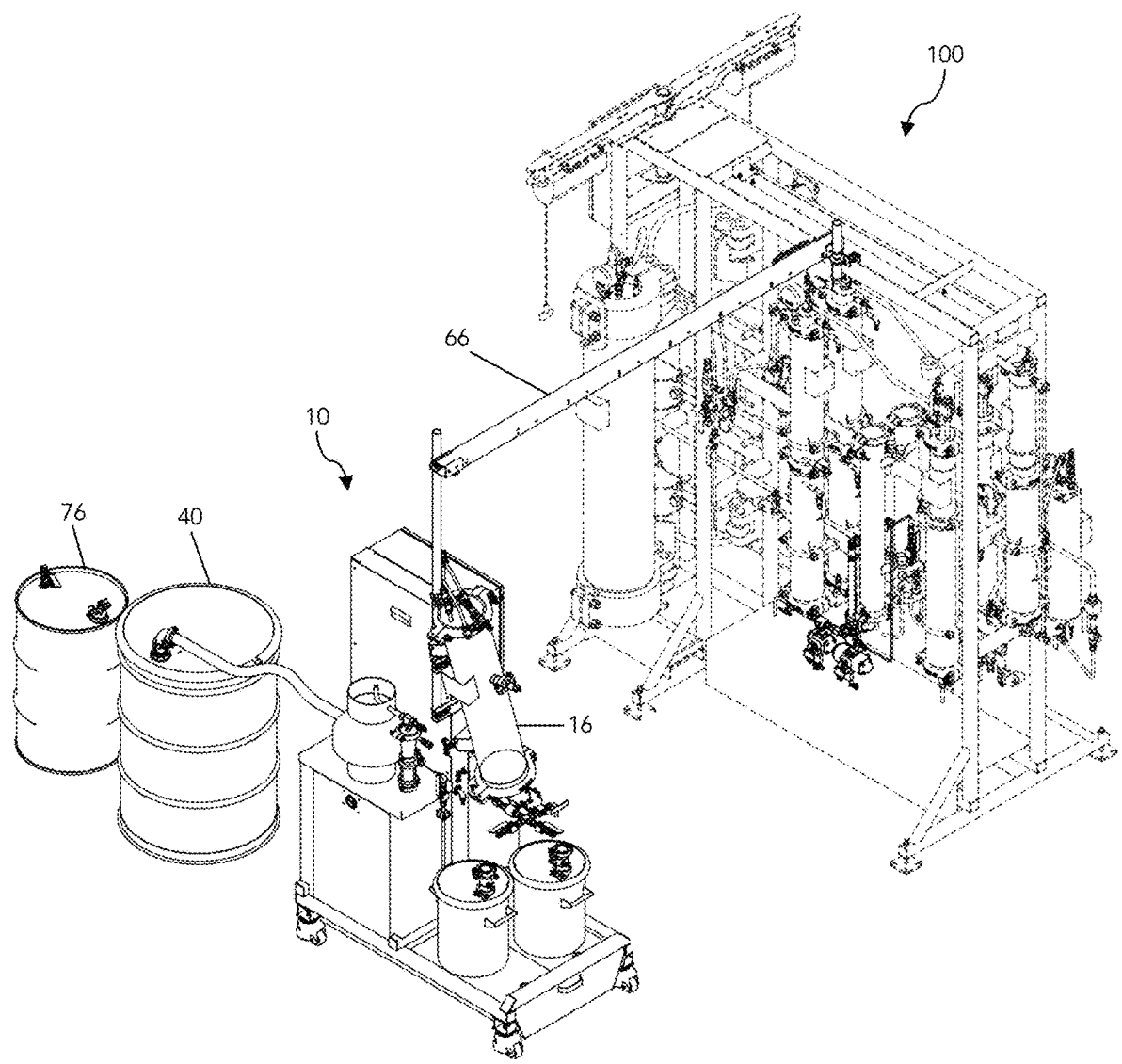
FIG. 11 is an isometric view of a cosolvent system integrated with a superfluid extraction system.

FIG. 11 is an isometric view of a cosolvent system fluidly connected to a superfluid extraction system. An overhead cable management system 66 can be provided to route high pressure process lines and controls cables from the superfluid cosolvent system 10 to the superfluid extraction system 100. Superfluid cosolvent system 10 shown comprises one secondary containment tank 40, which contains a cosolvent supply tank, and one mobile fill tank 76. Fluidly connected to the superfluid extraction system are cosolvent supply valves and separator collection valves. A three-way cosolvent supply valve can direct cosolvent into the superfluid extraction system or bypass the cosolvent to the collection line for cleaning and purging. The separator collection valves will only actuate when deemed safe and required by the control system either automatically or driven by the human machine interface. The collection valves open and allow for cosolvent and extractant to flow by means of differential pressure into the collection vessel 16. Optionally the control valves can open and transfer can be assisted by other means such as a pump, compressor, or vacuum system. The cosolvent system can be provided as an integrated component of a superfluid extraction system. Alternatively, the cosolvent system can be provided as a retrofit or add-on component of a superfluid extraction system with suitable high pressure integration.

Example 1—Recovery of Cannabinoids, Monosolvent Compared to Cosolvent Mixture

A baseline control of monosolvent extractions with only $CO_2$ was performed on both milled and un-milled pre-cooled dry biomass to compare the efficacy of the present cosolvent system under various conditions compared to extraction with a superfluid in the absence of cosolvent. In the first set of experiments, whole unmilled and milled dry hemp flower was extracted using the present system using multiple parameters to determine the efficacy of the extraction system under various conditions in the absence of cosolvent. Table 1 shows data from multiple monosolvent extractions in the absence of cosolvent. The average CBD mass extracted was 81.9% with an average CBD mass extracted per hour of 212 g/hr based on the column load. The resulting liquid monosolvent $CO_2$ extraction with no cosolvent collected a fraction high in terpenes and low in water and other impurities.

TABLE 1

Extraction of milled and unmilled hemp flower with liquid carbon dioxide monosolvent

| ID | Pressure (psi) | Extraction Temp (° F.) | Flow Rate (kg/min) | Moisture (%) | Milled | Run Time (min) | Input Mass (g) | % CBD Extracted | Average CBD Mass Extracted per Hour (g/hr) |
|---|---|---|---|---|---|---|---|---|---|
| 1 | 2700 | 70  | 4.5-5 | 15% | No  | 240 | 12961 | 73.40% | 214 |
| 3 | 2700 | 70  | 4.5-5 | 15% | Yes | 240 | 15044 | 79.90% | 215 |
| 7 | 2700 | 70  | 4.5-5 | 8%  | Yes | 240 | 14605 | 84.10% | 235 |
| 2 | 2700 | 140 | 4.5-5 | 15% | No  | 300 | 12430 | 89.50% | 150 |
| 4 | 2700 | 140 | 4.5-5 | 15% | Yes | 240 | 16091 | 79.00% | 270 |
| 6 | 2700 | 140 | 4.5-5 | 8%  | No  | 300 | 12718 | 91.40% | 172 |
| 8 | 2700 | 140 | 4.5-5 | 8%  | Yes | 240 | 14626 | 76.30% | 230 |

To test the effectiveness of adding a cosolvent to the extraction process, a second set of experiments was done to compare extraction efficiency. Whole unmilled hemp flower was extracted using the present superfluid extraction system and cosolvent system under various process parameters and cosolvent amounts as shown in Table 2.

TABLE 2

Cosolvent Extraction of unmilled hemp flower with liquid carbon dioxide and cosolvent

| ID | Extraction Pressure (psi) | Extraction Temp (° F.) | Flow Rate (kg/min) | Co-Solvent Flow Rate (kg/min) | Total EtOH Used (L) | Material | Run Time (min) | Input Mass (g) | % CBD Extracted | Average CBD Mass Extracted per Hour (g/hr) |
|---|---|---|---|---|---|---|---|---|---|---|
| RC02 | 2700 | 70 | 4.5-5 | 2% | 12.6 | 7.5% Unmilled | 90 | 11343 | 88.20% | 531 |
| RC03 | 2700 | 70 | 4.5-5 | 3% | 17.1 | 7.5% Unmilled | 50 | 12582 | 86.20% | 995 |

Figure 12A:
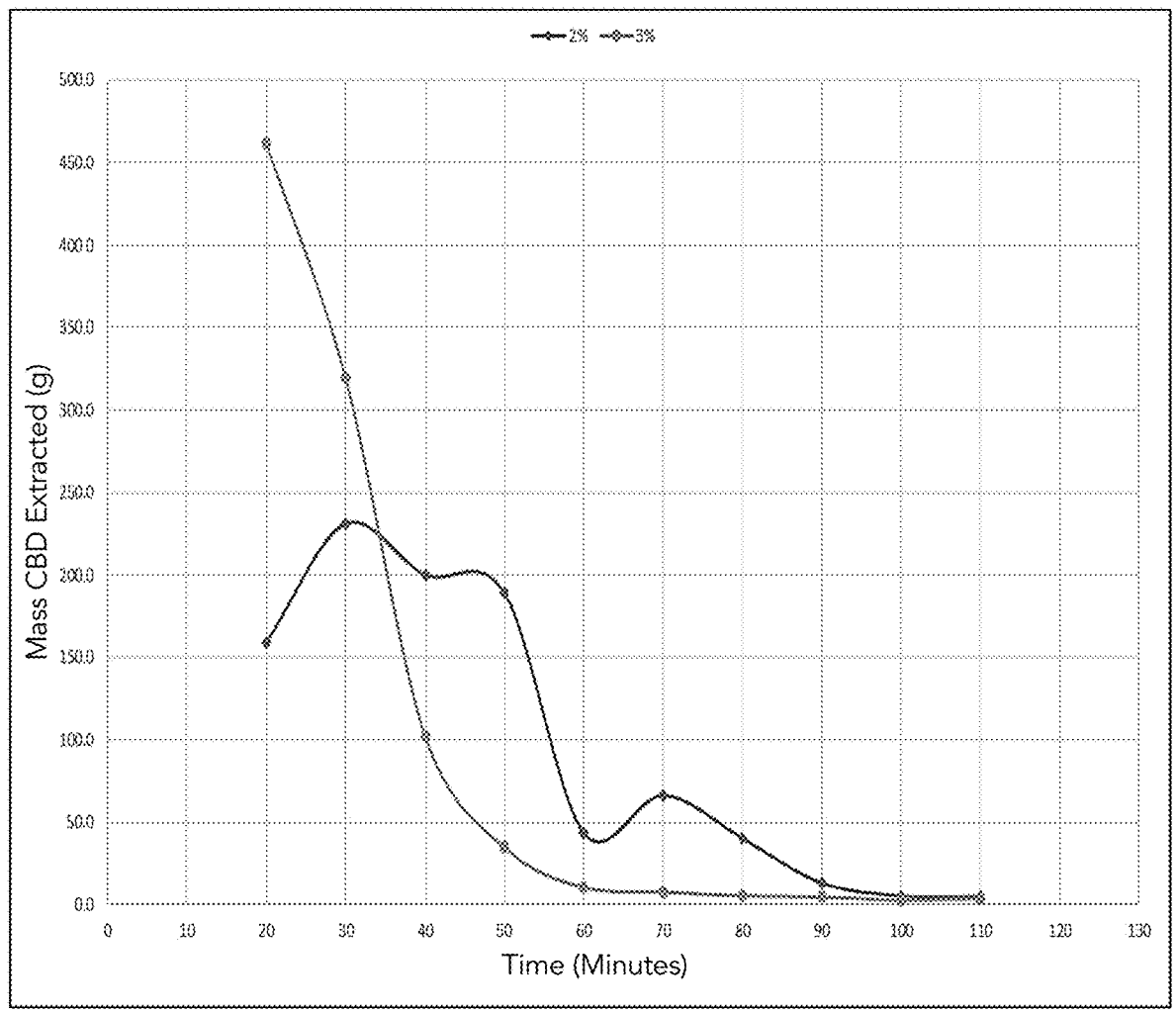
FIG. 12A graphically shows the mass of total cannabidiol (CBD) extracted for varying ethanol cosolvent flow rates from unmilled hemp flower.
Figure 12B:
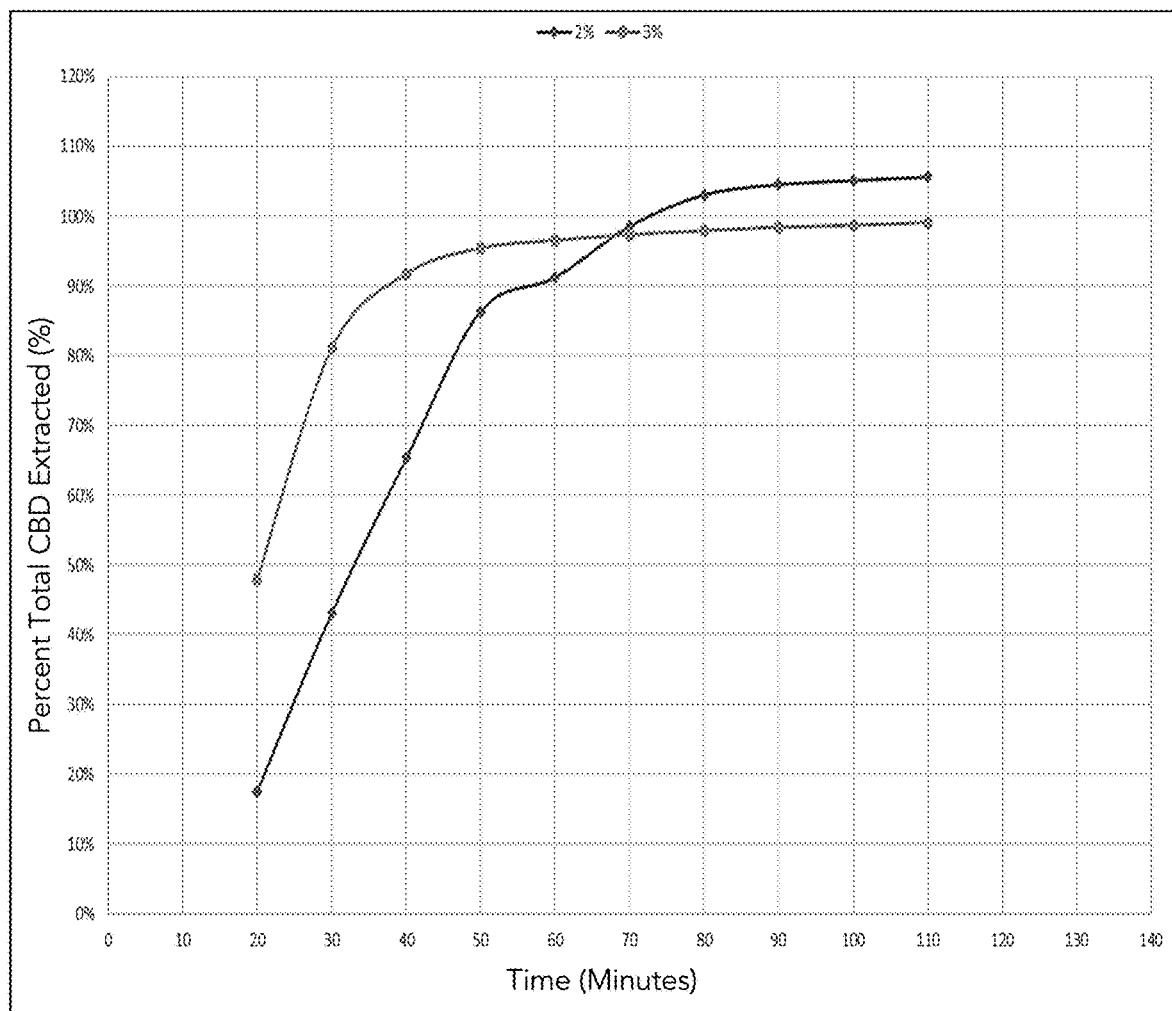
FIG. 12B graphically shows the percentage of total available CBD extracted for varying ethanol cosolvent flow rates from unmilled hemp flower.

FIG. 12A graphically shows the mass of total CBD extracted using a superfluid extraction process under varying ethanol cosolvent flow rates using unmilled hemp flower. FIG. 12B graphically shows the percentage of total CBD extracted using a superfluid extraction process under varying ethanol cosolvent flow rates from unmilled hemp flower.

Milled hemp flower biomass was also processed using multiple parameters to determine the efficacy of the cosolvent system under various conditions compared to whole flower. Table 3 shows the average mass of CBD extracted per hour based on a varying cosolvent flow rate using ethanol as the cosolvent at a constant cosolvent flow rate.

TABLE 3

Extraction of milled hemp flower with liquid carbon dioxide and cosolvent

| ID | Extraction Pressure (psi) | Extraction Temp (° F.) | Flow Rate (kg/min) | Co-solvent Flow Rate (kg/min) | Total EtOH Used (L) | Material | Run Time (min) | Input Mass (g) | % CBD Extracted | Average CBD Mass Extracted per Hour (g/hr) |
|---|---|---|---|---|---|---|---|---|---|---|
| A13 | 2700 | 70 | 4.5-5 | 1% | 5.7 | 7.0% Milled | 100 | 19710 | 80.60% | 661 |
| 1A | 2700 | 70 | 4.5-5 | 3% | 17.1 | 7.0% Milled | 80 | 17658 | 84.80% | 753 |

TABLE 3-continued

Extraction of milled hemp flower with liquid carbon dioxide and cosolvent

| ID | Extraction Pressure (psi) | Extraction Temp (° F.) | Flow Rate (kg/min) | Co-solvent Flow Rate (kg/min) | Total EtOH Used (L) | Material | Run Time (min) | Input Mass (g) | % CBD Extracted | Average CBD Mass Extracted per Hour (g/hr) |
|---|---|---|---|---|---|---|---|---|---|---|
| A18 | 2700 | 70 | 4.5-5 | 4% | 16.2 | 7.0% Milled | 70 | 18451 | 86.20% | 1034 |
| O21 | 2700 | 70 | 4.5-5 | 5% | 12.2 | 7.0% Milled | 40 | 15925 | 84.00% | 1343 |

Figure 13A:
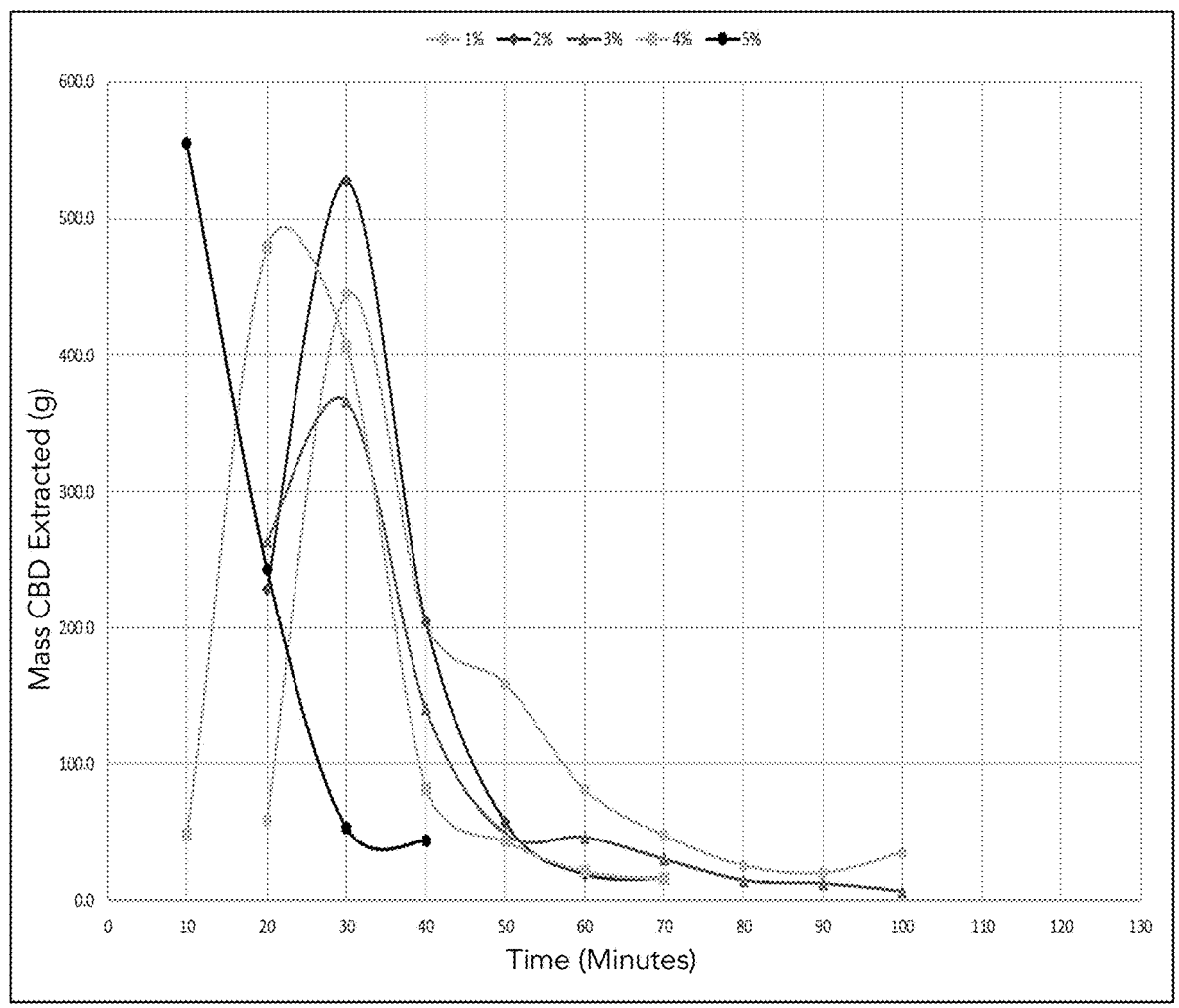
FIG. 13A graphically shows the mass of total CBD extracted for varying ethanol cosolvent flow rates from milled hemp flower.
Figure 13B:
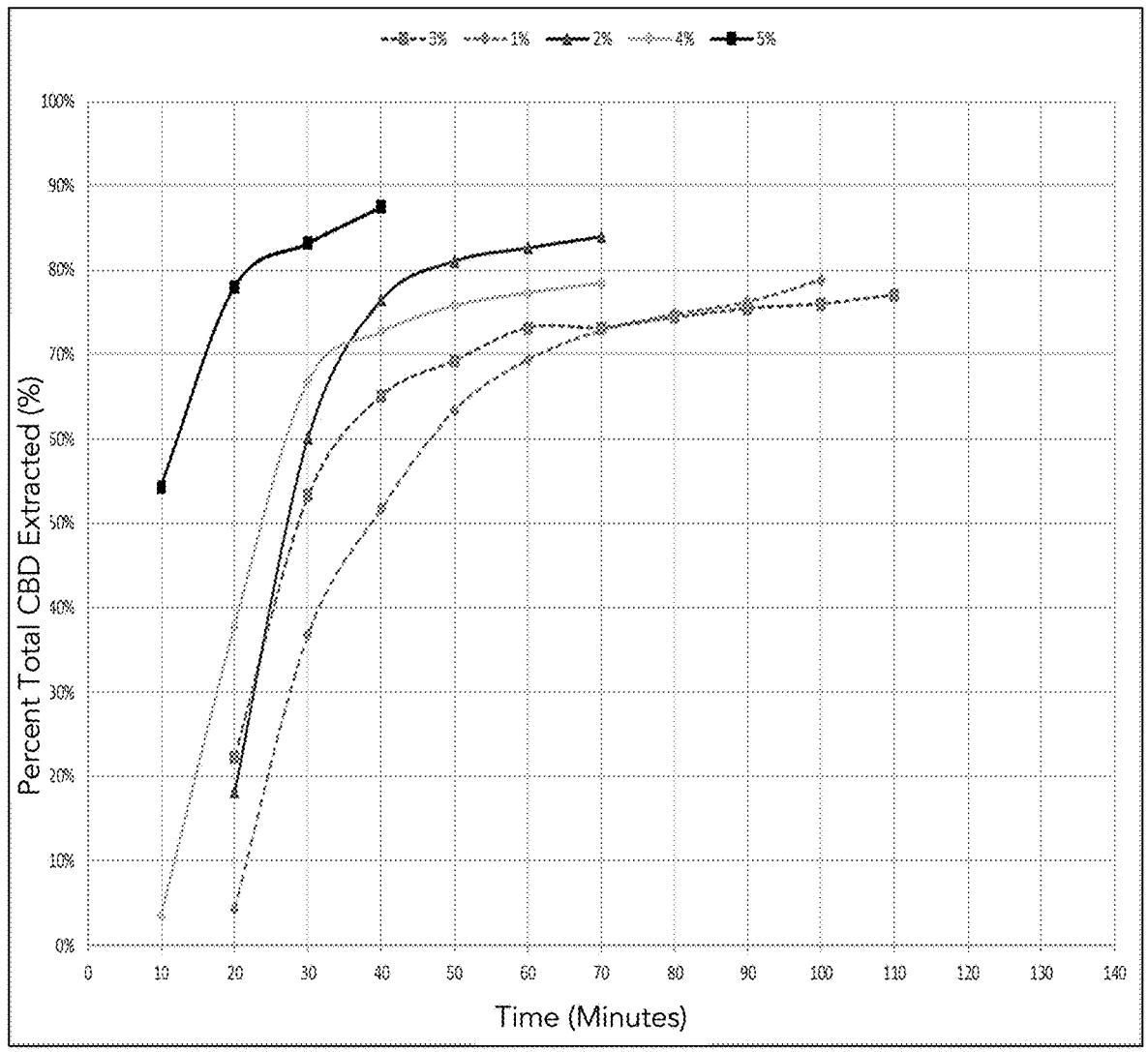
FIG. 13B graphically shows the percentage of total available CBD extracted for varying ethanol cosolvent flow rates from milled hemp flower.
Figure 13C:
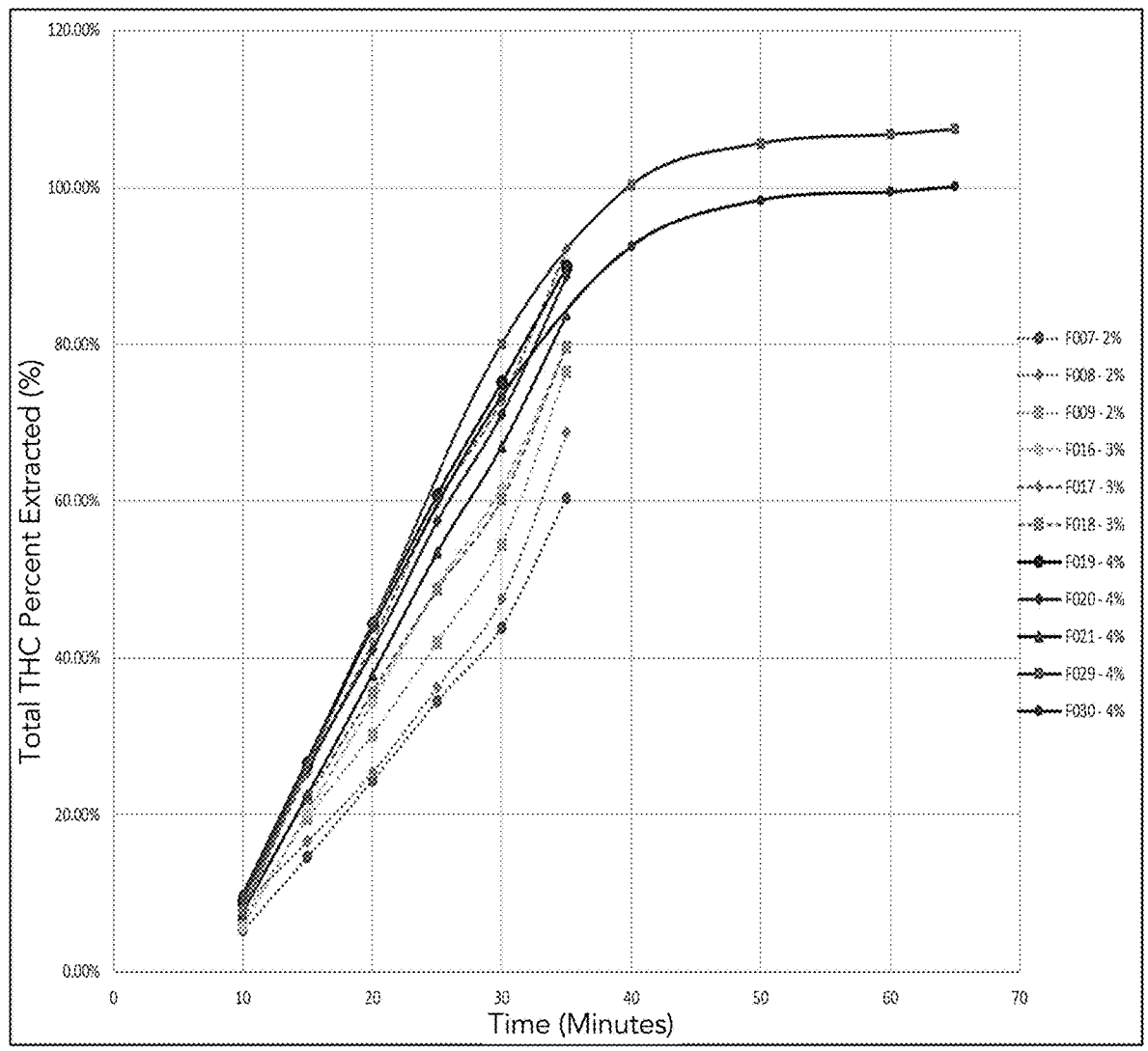
FIG. 13C graphically shows the cumulative percentage of total available THC extracted based on available THC for varying ethanol cosolvent flow rates from milled cannabis flower.
Figure 13D:
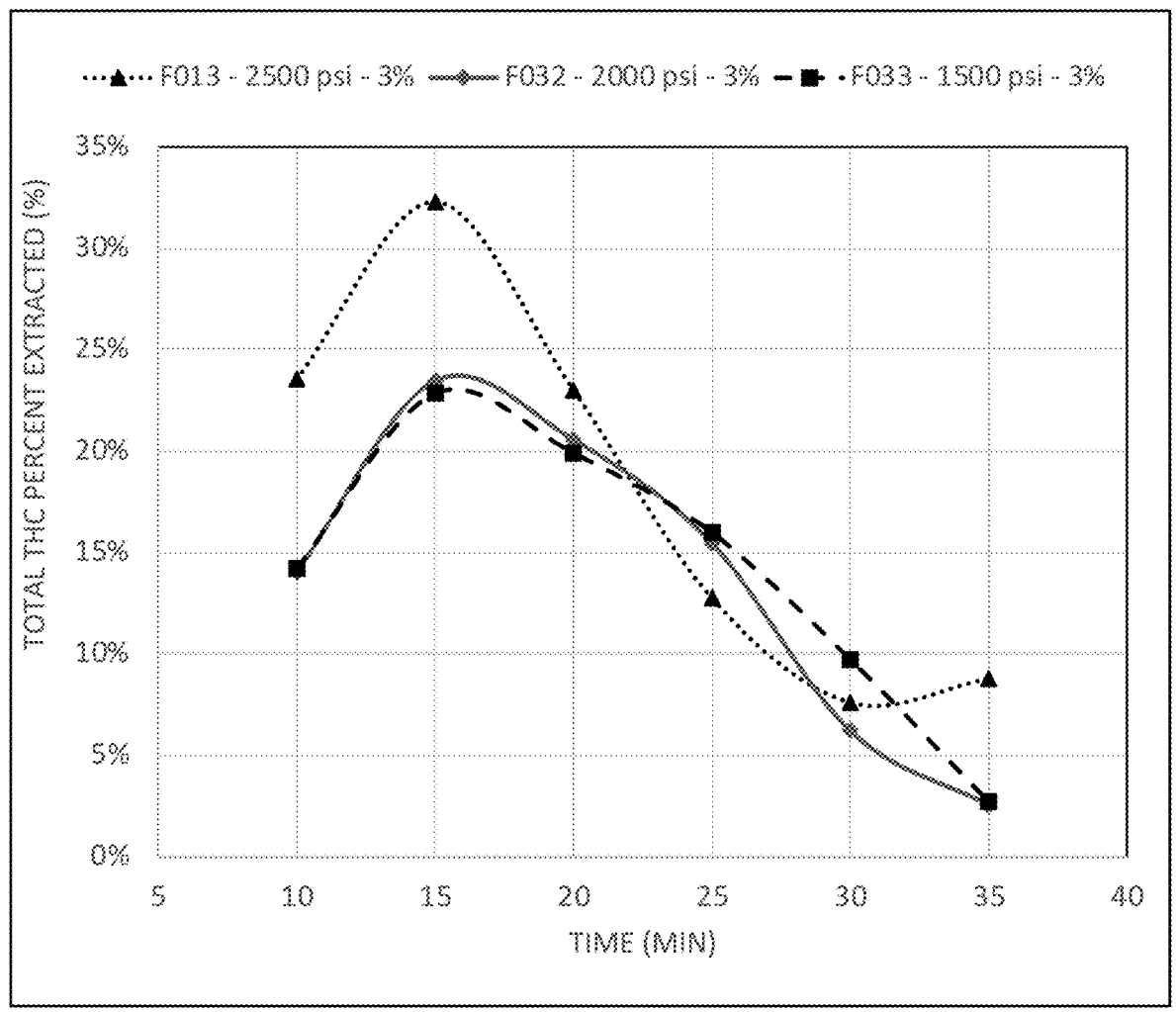
FIG. 13D graphically shows the percentage of total THC extracted for varying ethanol cosolvent flow rates from milled cannabis flower.

FIG. 13A graphically shows the mass of total CBD extracted using a superfluid extraction process under varying ethanol cosolvent flow rates from milled hemp flower. FIG. 13B graphically shows the percentage of total CBD extracted using a superfluid extraction process under varying ethanol cosolvent flow rates from milled hemp flower. FIG. 13C graphically shows the cumulative percentage of total THC extracted based on available THC for varying ethanol cosolvent flow rates from milled hemp flower. In this graph a 'scaled' solution is shown when extraction parameters are scaled according to the present method. FIG. 13D graphically shows the percentage of total THC extracted for varying ethanol cosolvent flow rates from milled hemp flower.

Figure 13E:
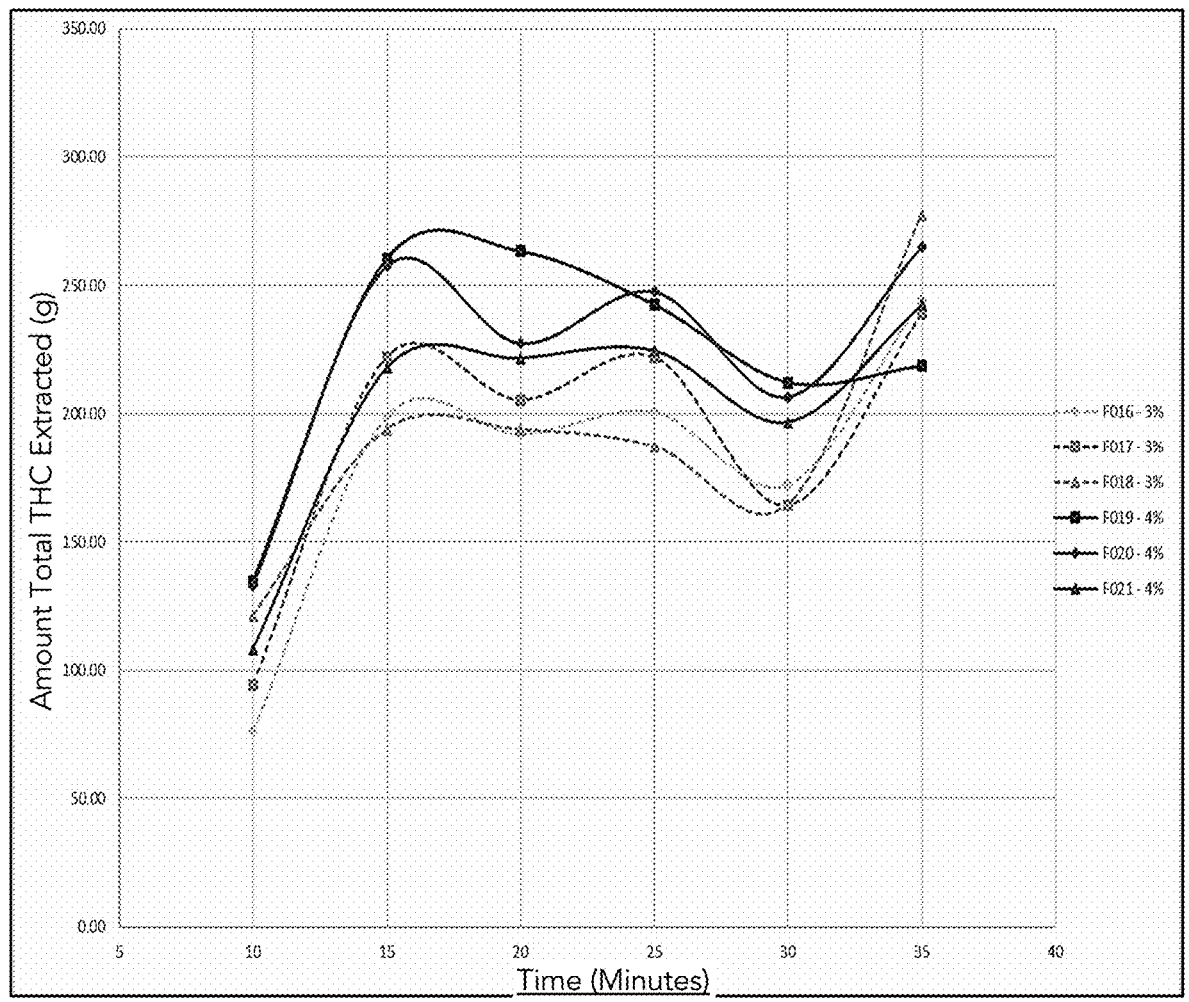
FIG. 13E graphically shows the mass of total THC extracted for varying ethanol cosolvent flow rates from milled cannabis flower.

FIG. 13E graphically shows the mass of total THC extracted for varying ethanol cosolvent flow rates from milled hemp flower. FIG. 13E shows the same data as FIG. 13C but in a non-cumulative form, and specific to a column which was loaded with 7500 g of biomass. Specifically looking at sample F019, at 10 min, 140 g THC was collected which represents 10% of available (FIG. 13C), and at 15 min 255 g was collected (395 g total) or 25% of available (FIG. 13C).

In another experiment, kief was processed using multiple parameters to determine the efficacy of the cosolvent system under various conditions. Kief comprises the resinous trichomes of cannabis that can accumulate in containers or be sifted from loose, dry cannabis infructescences with a mesh screen or sieve. Kief was extracted with in a superfluid extraction system with a cosolvent. In the experiments shown in Table 4, a sample comprising 4.2% CBD kief was run through the extraction system under various cosolvent conditions.

Figure 14A:
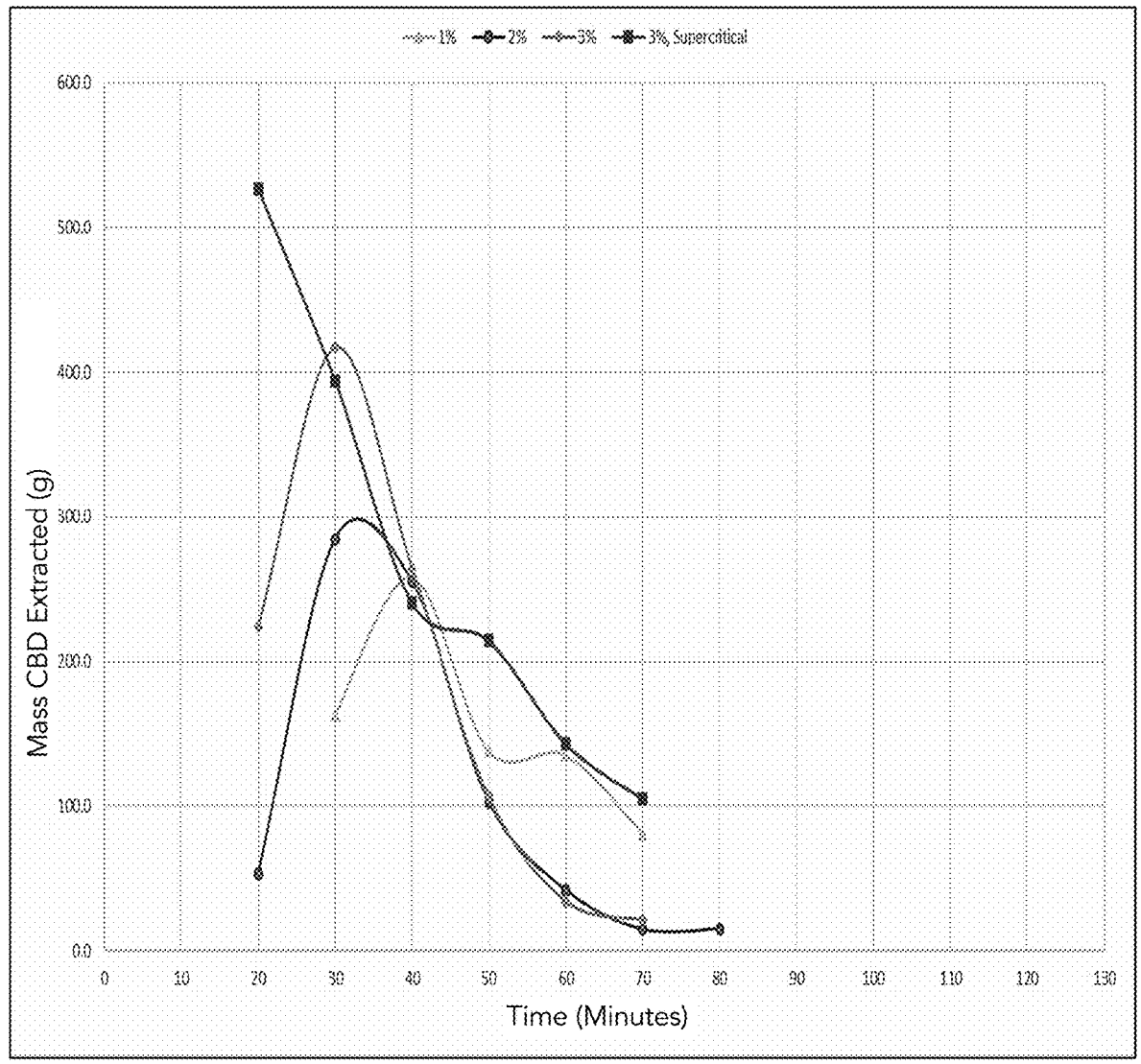
FIG. 14A graphically shows the mass of total CBD extracted for varying ethanol cosolvent flow rates from kief.
Figure 14B:
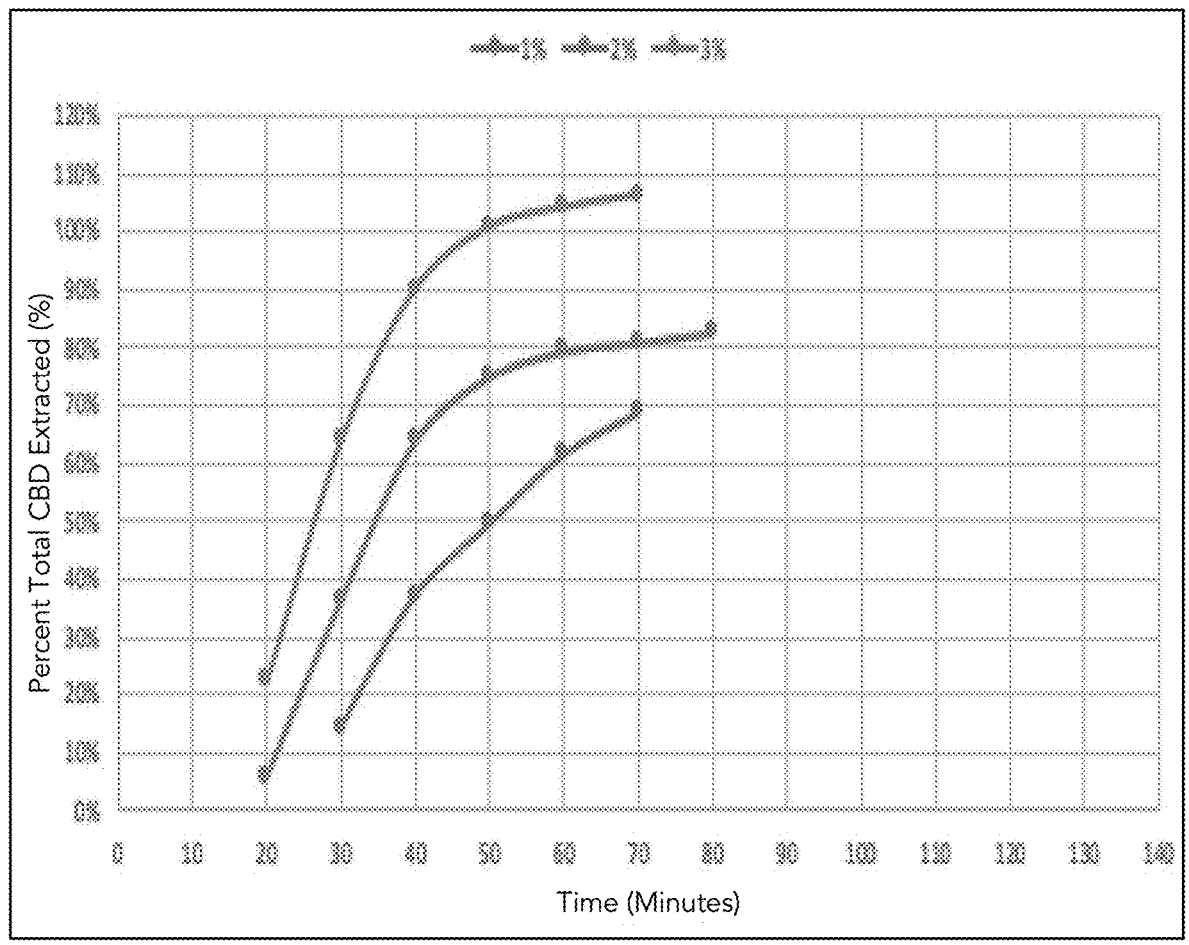
FIG. 14B graphically shows the percentage of total CBD extracted for varying ethanol cosolvent flow rates from kief.
Figure 14C:
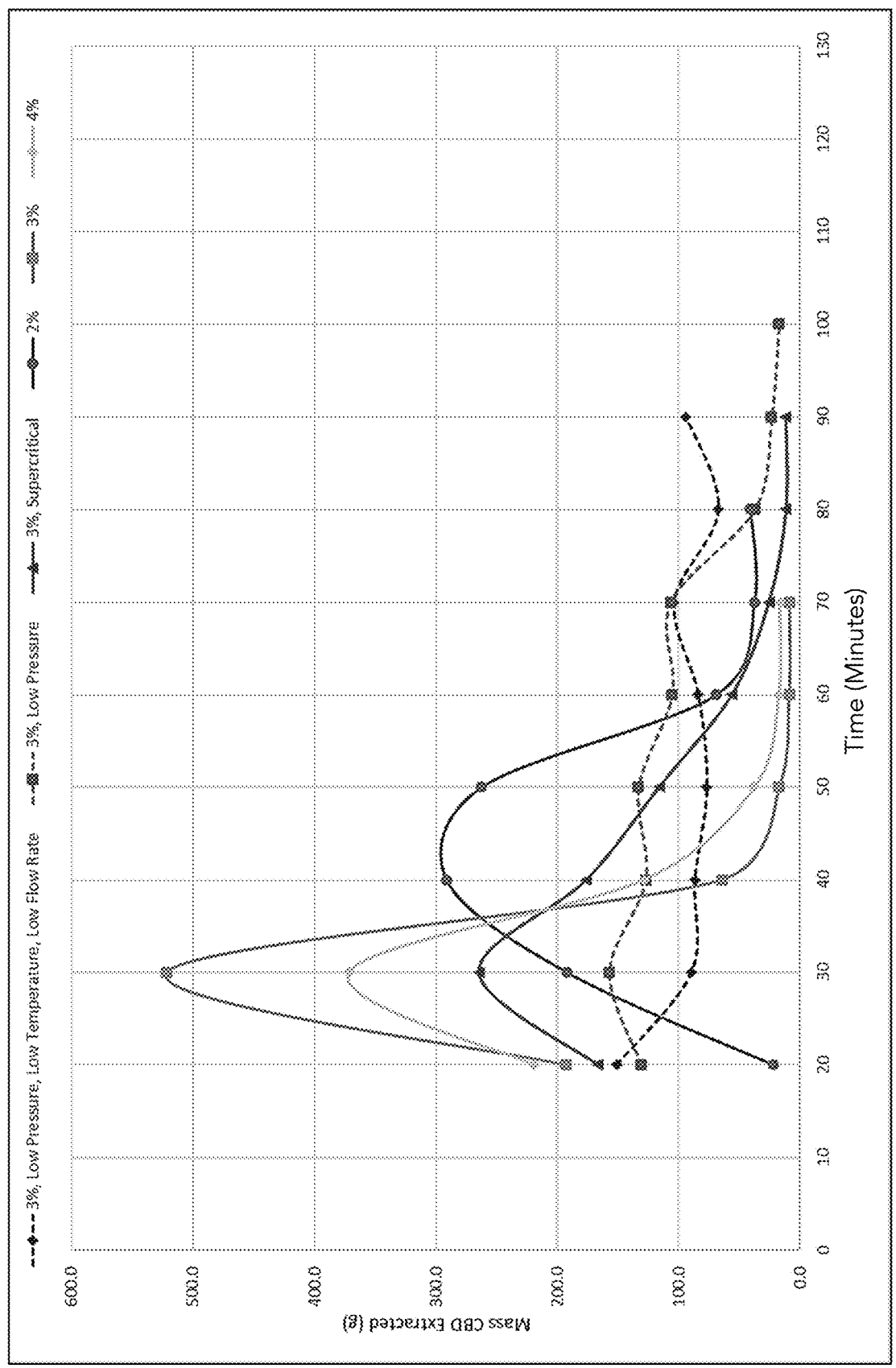
FIG. 14C graphically shows the mass of total CBD extracted for varying ethanol cosolvent flow rates from low potency kief.

FIG. 14A graphically shows the mass of total CBD extracted using a superfluid extraction process under varying ethanol cosolvent flow rates from kief. FIG. 14B graphically shows the percentage of total CBD extracted using a superfluid extraction process under varying ethanol cosolvent flow rates from kief. FIG. 14C graphically shows the mass of total CBD extracted for varying ethanol cosolvent flow rates from low potency kief.

Example 2—Recovery of Available Cannabinoids from Cannabis Biomass with Cosolvent System The present cosolvent system can be used for the recovery of available cannabinoids from cannabis biomass with sub-cooled liquid $CO_2$ and cosolvent for creating three primary extraction fractions of varying quality and cannabinoid potency. The method of extraction of the biomass is planned based on input parameters of the biomass as determined by analytical methods. It has been found that an extraction plan designed to capture three primary fractions consisting of 1) a first monosolvent high terpene fraction, 2) a second cosolvent high cannabinoid fraction, and 3) a third reclamation 'low quality' fraction results in an efficient process to obtain a high cannabinoid fraction of good purity. The second high cannabinoid fraction is a cannabinoid-rich extract which is substantially free of volatile terpenes and has a high content of cannabidiol (CBD & CBDA). Each of the fractions can be automatically dispensed and independently collected for bulk secondary processing of said fractions. The ratio of the cosolvent injected from the superfluid cosolvent system into the extraction system vs the $CO_2$ flow rate varies the solubility of the extracted compounds in solution affects the output of the extraction, optimizing the extraction process. For the case of ethanol as the cosolvent, ethanol is more polar than $CO_2$ and therefore has a higher affinity for cannabinoids, allowing it to achieve a more suitable solvent polarity for extracting cannabinoids. Therefore, the more ethanol added into the system the faster cannabinoids will be extracted, reducing extraction times.

TABLE 4

Extraction of kief with liquid carbon dioxide and cosolvent

| ID | Extraction Pressure (psi) | Extraction Temp (° F.) | Flow Rate (kg/min) | Co-Solvent Flow Rate (kg/min) | Total EtOH Used (L) | Run Time (min) | Input Mass (g) | % CBD Extracted | Average CBD Mass Extracted per Hour (g/hr) |
|---|---|---|---|---|---|---|---|---|---|
| RCKF3 | 2700 | 70 | 4.5-5 | 1% | 4.5 | 70 | 27499 | 82.70% | 802 |
| RCKF1 | 2700 | 70 | 4.5-5 | 2% | 9.5 | 70 | 22235 | 92.70% | 734 |
| RCKF2 | 2700 | 70 | 4.5-5 | 3% | 11.3 | 50 | 24434 | 87.60% | 1023 |

The ideal extraction scenario is a balance between faster extraction times (higher concentration of ethanol) and product quality (less undesirables in the oil). To maintain terpene quality it has been found that terpenes can be effectively collected with a superfluid monosolvent phase prior to starting cosolvent injection. To extract the terpenes with a subcritical $CO_2$ extraction, the terpenes can be collected through the manual drain valves on the cyclones, or optionally by directing the monosolvent terpene fraction to the collection vessel and collecting the fraction after depressurization. Once completed the cosolvent injection can commence.

Input cannabinoid-containing biomass material samples were analyzed using one or more analytical chromatographic method, such as high performance liquid chromatography (HPLC) or gas chromatography mass-spectrometry (GCMS), or thin layer chromatograph (TLC) to determine the total available cannabinoids, predominantly THC and isomers or CBD and isomers and total available terpenoids and aromatic molecules. Optionally the starting biomass sample can also be provided with a certificate of analysis which outlines the required information, optionally also with a proposed plan for extraction. The extraction time required for each fraction is dependent on available desired compounds, terpenes and cannabinoids respectively. The extraction and collection of the third and final reclamation fraction is dependent on the calculated cosolvent rate and total amount of cosolvent 'lag' in the system. Cosolvent lag' is the time required for the majority (99%+) of cosolvent to be collected from the extraction system, as calculated from the time of injection, through the extraction process, and dispensed from the process. In this example, a cosolvent is injected to the extraction system ahead of the phase management system and is blended with the primary solvent ($CO_2$). The injected cosolvent is dissolved into the primary solvent, making an extraction solvent solution, and travels through the process lines, the extraction column, and finally into the cyclone separator where it is removed from the process stream with the cannabinoids. The time for which the cosolvent travels through the system from injection point to collection point is a function of the primary solvent and cosolvent mass flow rates and the cumulative volume of the system between those points. The total primary solvent ($CO_2$) cumulative flow is measured in 'Column Volumes' which is defined as the total internal volume, unpacked, of the extraction vessel. For a 45 L extraction column, one 'column volume' (CV) is 45 L. With a fixed flow rate of 5 kg/min [m] (assuming a solvent density of near 1 kg/L) input solvent, one column volume of process time requires [CV]/[m]=9 min.

Various recommended $CO_2$ solvent density and flow properties based on a 20.3 cm (8.0 inch) column diameter are shown in Tables 5A-5D, which provide target parameters of linear column velocity as a function of $CO_2$ pressure, temperature, and mass flow under various extraction conditions. Table 5A provides example column conditions with a non sub-cooled extraction. In particular, under these conditions the biomass is not subjected to a cryogenic pre-freezing step prior to extraction and the extraction conditions are carried out at temperatures above 0° C. Table 5B provides example column conditions for an extraction process using cryogenically pre-frozen biomass during an extraction step. After preliminary cryo-freezing of the biomass to a temperature of 0° C. or less, the extraction can be carried out either with carbon dioxide monosolvent or with carbon dioxide mixed with cosolvent, or both in sequence, where the extraction process is maintained below 0° C. and optimally below −10° C. In a cannabinoid-rich biomass, this extraction step would provide the cannabinoid fraction. Table 5C provides example column conditions using cryogenically pre-frozen biomass during a monosolvent extraction at lower pressure, where extraction is maintained below 0° C. and optimally below −10° C. In a cannabinoid-rich biomass, this first monosolvent step in the extraction process would provide the terpene fraction. In a hops biomass containing alpha acids, such as flavonoids, as well as terpenes this step in the extraction process would provide the terpene fraction. In hops, flavonoids can be bitter and distasteful to some people, and it has been found that the present process is capable of separating out the hops flavonoids from the more appealing terpenes which provide more favorable aroma and flavor, while removing the flavonoids and bittering compounds of alpha acids, primarily humulene. Table 5D provides example column conditions using cryogenically pre-frozen biomass during a monosolvent extraction at lower pressure with fresh or dried hops biomass, where extraction is maintained below 0° C. and optimally below −10° C. In a hops biomass, this extraction process would provide the alpha acids and beta acid flavonoid fractions.

TABLE 5A

| P (psi)/T (F) | 850/50 | 850/50 | 850/50 | 2500/60 | 2500/40 |
|---|---|---|---|---|---|
| Mass Flow (kg/m) | 3 | 4 | 5 | 5 | 5 |
| Density (Kg/L) | 0.88 | 0.88 | 0.88 | 0.94 | 0.99 |
| Linear V (cm/min) | 8.14 | 10.85 | 13.57 | 14.49 | 15.26 |

TABLE 5B

| P (psi)/T (F) | 2000/0 | 2000/0 | 2000/0 | 2000/30 | 2000/30 | 2000/30 |
|---|---|---|---|---|---|---|
| Mass Flow (kg/min) | 3 | 4 | 5 | 3 | 4 | 5 |
| Density (kg/L) | 1.067 | 1.067 | 1.067 | 0.998 | 0.998 | 0.998 |
| Linear V (cm/min) | 9.87 | 13.16 | 16.44 | 9.23 | 12.31 | 15.38 |

TABLE 5C

| P (psi)/T (F) | 550/0 | 550/0 | 550/0 | 550/30 | 550/30 | 550/30 |
|---|---|---|---|---|---|---|
| Mass Flow (kg/min) | 3 | 4 | 5 | 3 | 4 | 5 |
| Density (kg/L) | 1.027 | 1.027 | 1.027 | 0.934 | 0.934 | 0.934 |
| Linear V (cm/min) | 9.50 | 12.66 | 15.83 | 8.64 | 11.52 | 14.39 |

TABLE 5D

| P (psi)/T (F) | 850/0 | 850/0 | 850/0 | 850/30 | 850/30 | 850/30 |
|---|---|---|---|---|---|---|
| Mass Flow (kg/min) | 3 | 4 | 5 | 3 | 4 | 5 |
| Density (kg/L) | 1.038 | 1.038 | 1.038 | 0.953 | 0.953 | 0.953 |
| Linear V (cm/min) | 9.60 | 12.80 | 16.00 | 8.82 | 11.75 | 14.69 |

The present method assumes a biomass column packing density of between about 100 g/L and 330 g/L of prepared material, dried 5%-20%, and having particle sizes between about 250-5000 microns. In plant biomass extractions an ethanol (ethyl alcohol) cosolvent of quality between 180-200 proof is preferred, more preferably of 190 proof or higher. The mass flow rate of cosolvent is determined using the mass flow rate of $CO_2$, desired cosolvent flow rate, and the cosolvent density based on desired column velocity at each stage of extraction. This method is also applicable to the use of other Class 3 solvents, such as acetone, methanol, and isopropyl alcohol. This method can also be adapted to use other FDA class 3 solvents and alternate extraction calculations can be done based on the properties of the selected cosolvent for planning the extraction.

The extraction parameters for crude terpene recovery from a cannabinoid containing biomass based on total available terpene concentration can be determined based on quantitative and analytical results. Table 6 provides a recommendation of the total amount of solvent required for extraction of more than 80% of available terpenes with low amounts of co-extraction. This recommended protocol had been found to yield very good results for formulation of finished products in the methods later described for post processing of extracted primary fractions. Table 6 shows the target linear column velocity and required column volumes for terpene recovery.

TABLE 6

Target Linear Column Velocity and Required Column Volumes for Terpene Recovery

| Terpene | CS (%) m/m | CLV (target) (cm/min) | Duration (CV) |
|---|---|---|---|
| 0%-1% | N/A | N/A | N/A |
| 1%-2% | N/A | 8 | 1 |
| 2%-4% | N/A | 10 | 1.25 |
| 4%-6% | N/A | 15 | 2 |

Determination of extraction parameters for selective extraction of desired fractions and limiting co-extraction of undesired compounds to achieve above 80% extraction efficiency can be achieved using cosolvent amount and other process controls. In addition, it has been found that in a 45 L extraction system a high level of extraction efficiency can be achieved within 30 minutes of secondary extraction parameter initiation or commencement of cosolvent injection. Similar scaled extraction efficiencies can also be achieved for larger systems. The system parameters are selective for cannabinoid extraction and low amounts of co-extraction of undesired compounds from the biomass like sugars, waxes, plant oils, and chlorophyll were observed in the high quality second fraction. The cosolvent rates (CS %), column linear velocity (CLV), and column volumes (CV) for each range of biomass are specific to $CO_2$ primary solvent extraction parameters of 2500 psi, and starting temperature between 40 F (4.5° C.) and 60 F (15.5° C.). Further, optimization of all parameters, specifically CS, CLV, pressure at start and throughout, and temperature at start and throughout, can be done to achieve the desired separation/extraction. Cannabinoid (CNB) percentage of total cannabinoid available for extraction can be removed from the extraction system by carefully controlling the percentage of cosolvent used, column linear velocity (CLV), and column volume (CV) at each stage of the extraction, as shown in Table 7.

TABLE 7

Example Extraction Conditions for Cannabinoid Recovery

| Biomass CNB % | CS (%) m/m | CLV (target) (cm/min) | Duration (CV) |
|---|---|---|---|
| 3%-7% | 2.75 | 10 | 2.25 |
| 7%-15% | 3.25 | 15 | 3.3 |
| 15%-25% | 4 | 15 | 3.3 |
| 25%-35% | 5, 4, 3 | 15 | 4 |

During the course of an extraction without cryogenic pre-freezing or total pre-freezing of the biomass, as thermal energy is removed from the column the extraction temperature generally exhibits a decreasing temperature trend with a final extraction temperature near 35 F (1.5° C.). The reducing temperature and subsequently reduced solvency capacity of the $CO_2$ is an important factor in maintaining low amounts of co-extraction of undesired compounds. Table 7 illustrates a recommended total amount of $CO_2$ and ethanol cosolvent required for extraction of more than 80% of available cannabinoids with low amounts of co-extraction. These recommendations have been found to yield good results for formulation of finished products in the methods later described for post processing of extracted primary fractions in a 45 L extractor.

Example 3—Cryogenic Pre-Treatment of Cannabis and Oil Extraction

A method for extraction of fresh cannabis flower directly from harvesting with no drying is described using liquid carbon dioxide as the extractant and optionally with one or more cosolvents. However, the cannabis biomass can also be pre-frozen using liquid carbon dioxide, or optionally nitrogen, or an equivalent cryogenic process, and once frozen the biomass can be optionally broken up into particles of approximately 1 cm square. The cannabis biomass can either be directly packed while frozen into an extraction column, or put into a storage container kept in a cooled environment for later processing. Alternatively, in a preferred process, the cannabis biomass can be packed fresh, without pre-freezing or drying, directly into the extraction vessel or extraction column. In the loaded extraction vessel, liquid superfluid such as liquid nitrogen or liquid $CO_2$ can be used to lower the temperature of the biomass directly in the extraction column. As another alternative, dried flower can be packed directly into the extraction column, however it is observed that the drying process can lead to degradation of valuable sensitive and fragile compounds such as terpenes, and drying has been found to change the cannabinoid levels as compared to while the plant is still in a growing environment. In addition, the drying process for cannabis can be susceptible to pathogen and mold formation. The present process is capable of processing a wide range of biomass types depending on the requirements of the harvest, pre-processing conditions, and desired product, including fresh unprocessed biomass.

The extraction column and biomass is then fully frozen in a cryogenic pre-cooling step by evaporative cooling of the superfluid, preferably with liquid $CO_2$ below 0° C., and optimally below −10° C., directed toward the inlet of the extraction column. As liquid $CO_2$ fills the column while maintaining an inlet temperature below 0° C. and optimally below −10° C., the liquid $CO_2$ is boiled by absorbing heat from the biomass. The liquid $CO_2$ will boil at the saturation temperature defined for the maintained pressure of the column. As the $CO_2$ vapor travels through the column, the vapor further cools the biomass located above the liquid saturation line where all energy from the biomass has been removed. During the cryogenic pre-cooling step, the extraction column is preferably maintained at pressures below about 500 psi (3.45 Mpa) and more preferably below about 350 psi (2.4 Mpa) while the extraction column is filling with liquid $CO_2$ to freeze the biomass prior to extraction. A sensor instrument for detecting liquid or temperature probe at the column outlet can be used to identify when liquid $CO_2$ has reached the top of the column and the biomass is completely sub-cooled. During the direct refrigeration process for sub-cooling the biomass, the $CO_2$ is preferably recovered and recirculated from the top of the extraction column, or optionally vented to the atmosphere. Once the biomass is frozen, the $CO_2$ extraction process can begin.

Once the extraction column is full of cold liquid $CO_2$ and the biomass is frozen and sub-cooled, $CO_2$ circulation for extraction can begins with cold liquid $CO_2$ below 1100 psi (critical point) and optimally closer to 600 psi, or between about 400-800 psi. Liquid sub-cooled $CO_2$ is then directed over the biomass while maintaining an inlet and discharge temperature below 0° C. and optimally below −10° C. at a flow rate between 0.1 and 1000 kg/min, targeting a linear column velocity of up to 1000 cm/min, and optimally in the range of 7 cm/min. Liquid monosolvent $CO_2$ is circulated through the extraction column and terpenes are collected in the cyclonic separation vessel as the first fraction. This full spectrum terpene fraction is free of any cosolvent and requires no post processing. Optionally the extractant is flowed through a process superheater which manages the $CO_2$ solution phase entering the separator allowing for rapid decompression and recirculation of the $CO_2$ and clean separation of the desired extractants.

In a second extraction step liquid $CO_2$ is circulated over the biomass and cannabinoids are collected from the extraction column in a cyclonic separation vessel with the subsequent fraction(s) of either $CO_2$ monosolvent or $CO_2$/cosolvent eluent fractions. In a cosolvent extraction various cosolvents can be used at various % mass relative to the liquid $CO_2$ depending on the type and constituents of the biomass and desired process results. Solvent free fractions (when only used with $CO_2$) are directly ready for consumer products or further processed and formulated into other products. It has been found, however, that extraction of biomass with liquid $CO_2$ monosolvent only will provide extractant fraction with higher amounts of waxes that need to be removed in secondary processing such as by filtration or winterization. In contrast, pressure-controlled liquid $CO_2$ monosolvent extraction followed by liquid $CO_2$ cosolvent extraction can reduce the amount of time required for the extraction and increase the solvent affinity for cannabinoids, thereby reducing the energy and solvent expenditure of the process. After a first pass extraction of terpenes with $CO_2$ monosolvent, biomass extraction to collect cannabinoids with $CO_2$ and a cosolvent in a second step takes about 30 minutes, whereas the same extraction takes 6 hours with $CO_2$ monosolvent with much higher percentage of wax in the extracted fraction. Therefore, a $CO_2$-cosolvent extraction step following a $CO_2$ monosolvent extraction step is preferably used to extract the cannabinoids remaining in the biomass. Optimally for fresh biomass material with moisture above 15%, a cosolvent is used which is immiscible with water with high selectivity for cannabinoids, and preferably a class 3 solvent. A variety of cosolvents may be used, including but not limited to ethanol, ethyl acetate, isopropyl alcohol, and acetone. It has been found that when the moisture content of the biomass is greater than 15%, advantageous to use a water-insoluble cosolvent to prevent coextraction of water soluble species. Less than 15% moisture content can use solvents that are water soluble such as acetone (better selectability for cannabinoids) or ethanol.

The extractants comprising liquid $CO_2$, optionally cosolvent, cannabinoids, carotenoids, alkaloids, and terpenes can be collected in cyclone separators and optionally automatically discharged to a high pressure cosolvent collection vessel. Cosolvent solutions can then optionally be directly winterized through a solvent cooling and filtration process, and/or processed with a filtration or nanofiltration process where waxes and impurities are removed from the extractant. The winterization process is a post-extraction step that removes waxes and less soluble material from an extractant oil by concentrating the extract solution and cooling it to a temperature at which waxes and lipid components precipitate, typically at around −40° C. In one example process cosolvent solution can be dewaxed or filtered, then passed through a nano-filtration membrane where the ratio of cosolvent in the solution is reduced. The reduced cosolvent solution is then further heated to evaporate the remaining cosolvent form the solution to leave the desired product. The cannabinoid fraction can then be recombined with the full spectrum terpene fraction which is free of solvent.

Figure 15:
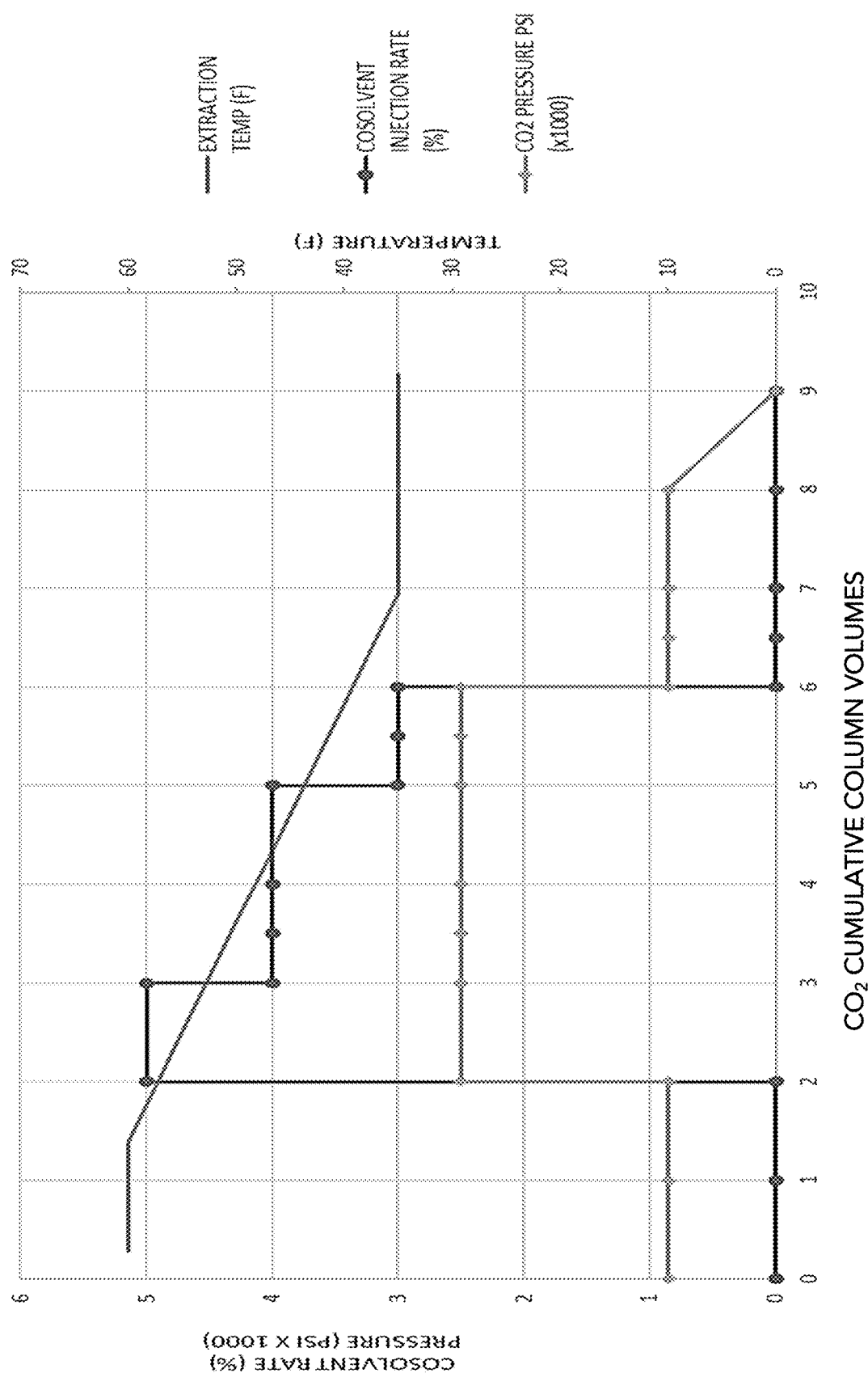
FIG. 15 graphically shows a sample extraction method for high cannabinoid and high terpene biomass using a controlled superfluid cosolvent system.

FIG. 15 graphically shows one sample step function extraction method for high cannabinoid and high terpene biomass extraction using a cosolvent process but without a preliminary biomass cryo-freezing step. Ramped solvent extractions and combinations of ramp and step methods can also be used and controlled by present cosolvent control system. As shown, the cosolvent rate and pressure injected into the extraction system is adjusted throughout the method to create conditions for extracting the desired fractions. In the system, the $CO_2$ extraction apparatus accumulators are conditioned so that the stored liquid $CO_2$ is below −17° C. (0° F.) and in a saturated liquid state or sub cooled state (306 psi or higher, but less than 350 psi). Liquid $CO_2$ is pumped into the system and into the packed extraction column at low pressure (accumulator pressure +50 psi typically) until liquid $CO_2$ fills the extraction column. Liquid $CO_2$ then enters the extraction column between −10° C. to 15° C. and liquid $CO_2$ boils to vapor as it travels through the extraction column, for a minimum pumped solvent of 1 column volume (CV). $CO_2$ then exits the extraction column and enters the separator series as a liquid, carrying some extractants with it. The pressure in the extraction column is then increased to 850 psi (+/−10%) and refrigeration maintains the liquid $CO_2$ in a subcooled state. Throughout the process $CO_2$ can be recycled and cooled directly by refrigerant evaporating, for example at −20 C. When liquid $CO_2$ reaches the cyclone separators, the cumulative flow for terpene extraction is commenced based on above determined parameters; this is considered point of 0 CV for the method. The extraction process pressure is then increased to 2500 psi within 5 minutes and cosolvent injection commences based on the above determined parameters as shown in FIG. 15. The same or similar recipe or process can be used to 99% or greater of all cannabinoids from a cannabinoid biomass. Cannabinoids as a general class of molecules extract in a similar fashion to THC and CBD, and it is understood that different cannabinoids can be extracted using similar procedure with similar results. Further different biomass samples can have different amounts, types, and ratios of cannabinoids. Based on the biomass samples that were provided, the total THC and/or CBD collected with these samples indicates that the same or similar procedure can be used with a broad range of biomass sources to collect cannabinoids.

The first primary monosolvent terpene fraction collection occurs at about ¼ column volume after completion of the recommended extraction duration. In the example shown in FIG. 15, terpene collection would occur at about 2.25 column volumes (CV) as calculated from the recommendation of Table 6 for 2 CV and +¼CV. The first monosolvent high terpene fraction can then be discharged from the cyclone separator in the extraction system and is preferably directed to the cosolvent system and cosolvent collection vessel. The collection vessel can be depressurized in a controlled manner to collect the terpene fraction and expel the $CO_2$ solvent, preferably recycling the bulk of the $CO_2$ solvent back into the extraction system. The terpene fraction can then be stored separately from where cosolvent cannabinoid fractions will be stored for further processing. At the completion of the terpene extraction, pressure in the extraction column is increased to 2500 psi (+/−10%). At about two column volumes of experiment duration the cosolvent begins injecting from the solvent system into the extraction system at a rate of 5% by mass of the bulk $CO_2$ solvent. At 3 CV, cosolvent rate is reduced to 4%, and at 5 CV, the cosolvent rate is reduced to 3%. At 6 CV, cosolvent injection is stopped, and the second cosolvent high cannabinoid fraction is discharged from the extraction system into the collection vessel of the cosolvent system. The cosolvent system then depressurizes the collection vessel to remove and recycle the $CO_2$ solvent from the second fraction and directs the second cannabinoid fraction into a second collection tank for secondary processing, separate from the first fraction.

At 6 CV the extraction pressure is reduced to 850 psi to begin solvent reclamation from the biomass. At 8 CV the reclamation process is complete and the extraction chamber begins to depressurize. At 9 CV the extraction process is complete and the third fraction is discharged from the cyclone in the extraction system into the cosolvent collection vessel. The cosolvent system then depressurizes the collection vessel and directs the third fraction into a third collection tank for secondary processing, separate from the first fraction and the second fraction, respectively. The $CO_2$ from the extraction process is recycled to the accumulators.

Secondary processing of crude fractions can then be carried out to obtain the desired products. Once the three fractions have been separated as described, further processing can be done to purify the fractions or further fractionate them into pure oil compounds. One example method is described herein, however it is clear that secondary processing of each of the fractions can be designed according to the requirements and production goals of the process. In this example, to purify the first monosolvent high terpene fraction, the fraction is distilled using vacuum assisted evaporation to collect the 'heads' of the fraction (terpenes) and store that collection as a cannabis derived terpene solvent, also referred to as fraction F1a. The tails of this first fraction of the first monosolvent high terpene fraction which mostly comprise cannabinoids are collected, referred to as fraction F1b. This high-cannabinoid fraction is optionally combined with the third crude reclamation fraction for further processing.

The second cosolvent high cannabinoid fraction is chilled to below −40° C. and held below −40° C. for more than 30 minutes. The chilled solution then flows through a series of filters which progressively decrease in micron rating from 40 μm to 0.5 μm. The chilled and filtered cosolvent solution is then desolvated to remove any residual cosolvent through evaporation, which is optionally possibly vacuum assisted to prevent the decarboxylation of cannabinoids, so that the final solution product is below 4500 ppm cosolvent. The resulting oil product is a cannabinoid primary fraction with potency above 80%, which is referred to as fraction F2a. Fraction F2a can also be optionally combined with the cannabis derived terpene solvent as described above, for example in a ratio between 20F2a:1F1a and 4F2a:1F1a. As would be understood, the final desired product or mixture can be widely varied depending on the desired properties, characteristics, and use of the product. The dewaxing process and solvent recovery process are optionally performed in-line with the cosolvent collection vessel and executed by circulating the cosolvent extractant through a series of nano-filtration membranes with a specified molecular weight cutoff. In one example, a first pass for dewaxing, the cosolvent extractant flows through a membrane which has been conditioned for the specific cosolvent where waxes are concentrated on the retentate of the process and cannabinoids and solvent are permeated and concentrated as they pass through the membrane. This molecular weight cutoff for the dewaxing application is typically between 400-500 angstroms. As a secondary step the dewaxed permeate can be processed with a smaller membrane in the range of 100-200 angstroms for the purposes of concentrating the cannabinoids on the retentate side of the membrane and allowing small impurities and solvents to permeate through the membrane. The in line membrane solution is preferred for operator safety as a closed system where there is no open pouring or transfer of solvents and extractants in the production process. The resulting products from an in-line membrane application can be treated the same as conventionally produced dewaxed oil through a thermal precipitation and filtration process.

Fraction F2a can also be optionally placed into a deep vacuum oven at 45° C., for example for more than about 30 minutes and less than about 24 hrs, and also be allowed to flow in a flat tray forming a thin layer between 0.5 and 3 mm thick. After 24 hrs from when the solution has reached a consistent thickness across the tray, heat and vacuum can be returned to ambient conditions and this finished product can be broken into hard pieces for use and/or storage. Fraction F2a can also optionally be dissolved into an organic solvent, for example pentane, and be allowed to homogenize between 40° C.-60° C. so that fraction F2a is fully dissolved in the solvent. The solvent can then be removed slowly to allow and encourage cannabinoid acid crystallization through desolvation, optionally under vacuum purge conditions. The solvent is then fully purged in a vacuum oven and the remaining cannabinoids crystals can be harvested or broken into pieces for use or storage, and optionally combined with fraction F1a. Optionally, fraction F1a can be stored in a sealed container and allowed to self-crystalize where cannabinoid acid forms such as CBDa and THCa begin to group and form solids with covered by other dissolved cannabinoids and terpenes. It has been observed that storage for longer than a few days, such as a week or more, and preferably at least 4 weeks, can result in crystallization of cannabinoids from the F1a fraction. Other conditions for crystallization can also result in crystallized material from this sample fraction.

The third reclamation fraction, with optional addition of solids (tails) from fraction F1b, can be blended and then passed through a series of filter material, which may include but is not limited to filter cloths of various porosity, materials having pore sizes down to 0.5 µm, magsil, activated carbon, diatomaceous earth, bentonite, or other filter materials or media, or combinations thereof. These filtration devices and media can also act as color remediation media to remove the color from the material. This filtered solution is further referred to fraction F3af. Fraction F3af solution can then be chilled to below −40° C. and held below −40° C. for more than 30 minutes. The chilled solution can then be processed by flowing it through an additional series of filters which progressively decrease in micron rating from 40 µm to 2 µm. The chilled and filtered cosolvent solution is then desolvated to remove any residual cosolvent by evaporation, which is optionally vacuum assisted to prevent the decarboxylation of cannabinoids, so that the final solution is below 4500 ppm cosolvent. Optionally, fraction F3af can be further processed by a reactor where it is heated above 150 C at minimum 200 mbar of pressure and residual solvents reach levels below 500 ppm. The acid forms of cannabinoids will also decarboxylate in these conditions and form a high cannabinoid oil which is ready for distillation. This decarboxylated fraction is referred to as F3afd. Optionally fractions F3afd or F1a can be further processed using a molecular distillation process to produce high cannabinoid distillate solutions. Typically these distillate solutions are dominant in either THC or CBD depending on the biomass used for creation of the primary fractions.

Figure 16:
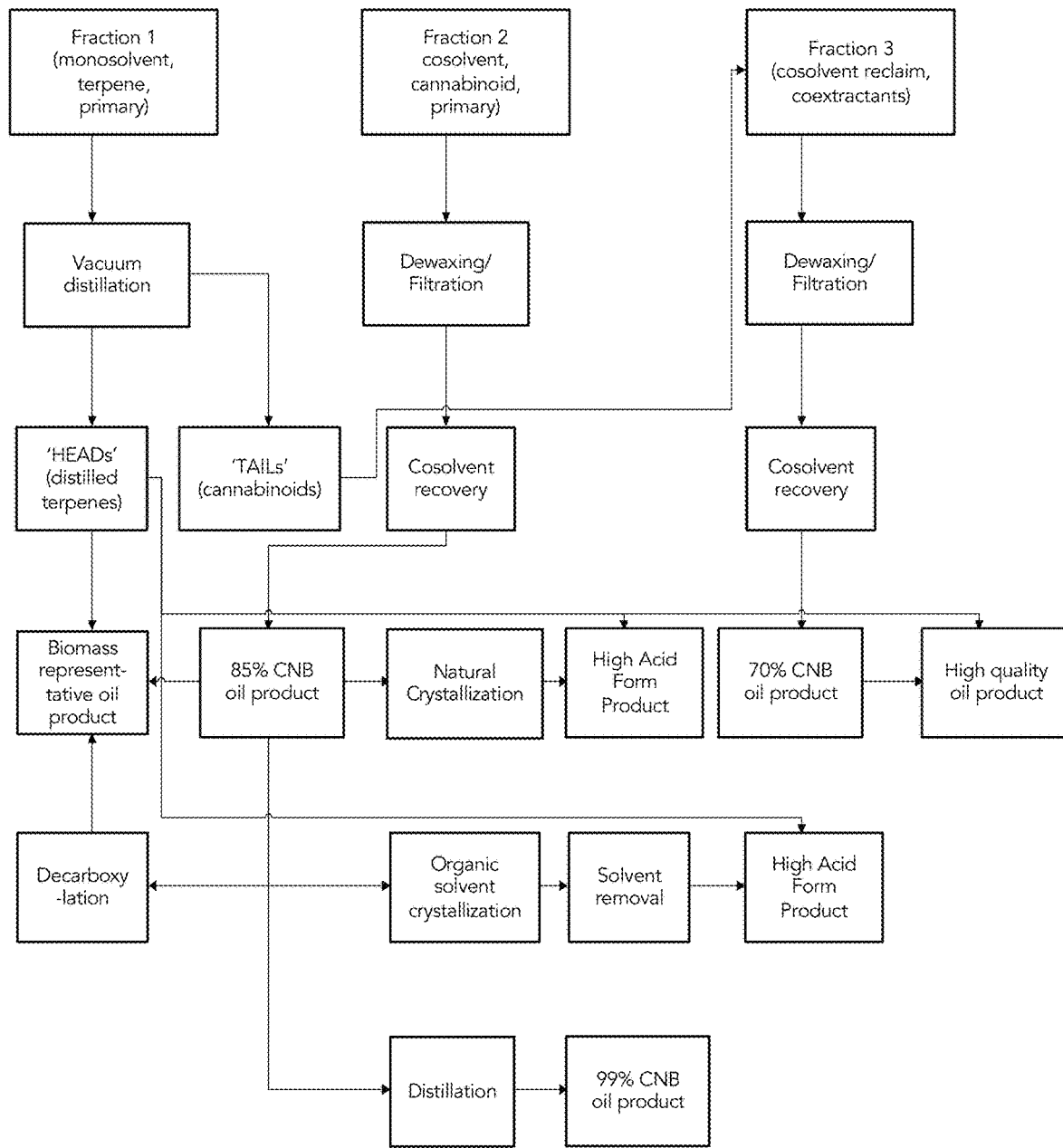
FIG. 16 is a processing flowchart for cannabis biomass extractant fractions.

FIG. 16 is an example of a processing flowchart for cannabis biomass extractant fractions with superfluid $CO_2$. Various secondary extraction and purification processes are known and available depending on the starting material and desired properties and purity of the recovery product. A first fraction (Fraction 1) is obtained with a $CO_2$ monosolvent extraction to obtain a terpene-rich fraction. It is understood from chromatographic methods that the composition of each fraction removed will be different depending on the conditions of the extraction, solvent used, and time that the fraction is isolated during the extraction, where time can be measured in, for example, duration, column volumes, or fraction volume. Once the $CO_2$ is mixed with cosolvent a second fraction (Fraction 2), or set of fractions, comprises the cannabinoids, with 70+% of cannabinoids extracted out in high purity. In a third reclamation fraction (Fraction 3) the biomass is extracted with $CO_2$ monosolvent to remove any excess cosolvent as well as to extract any residual valuable products. Removal of $CO_2$ and cosolvent from the collected fractions has been found to yield extraction of up to 99% of the cannabinoids in a cannabis biomass. A ratio of cannabis biomass mass to cosolvent of 1 kg cannabis to about 6-15 L ethanol cosolvent has been found to be highly effective in extracting out the majority (95%+) of cannabinoids from the biomass in Fraction 2 according to the present method. This is compared to an ethanol-only extraction of cannabis which requires about 35 L ethanol for every 1 kg cannabis to achieve a similar extraction efficiency. The present process is thus able to reduce the amount of solvent required to obtain the same or better extraction efficiency as organic monosolvent alone. In a cold process where biomass is initially frozen in a cooling step prior to extraction the chlorophylls also largely remain in the biomass during the extraction limiting chlorophyll contamination of the valuable terpene and cannabinoid fractions and thereby limiting post-processing required for the extractant oils.

Figure 17:
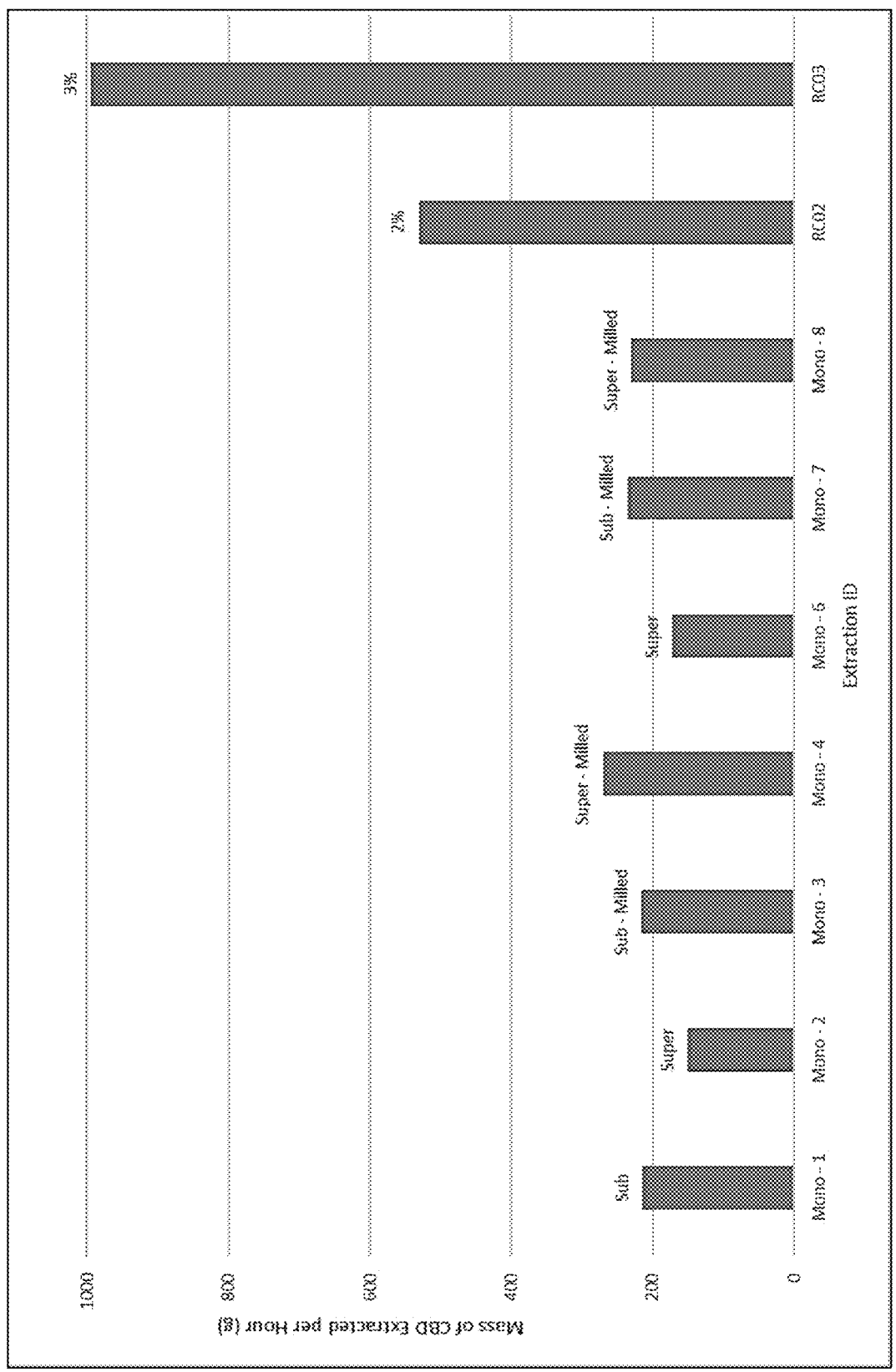
FIG. 17 is a line graph of the mass of CBD extracted per hour for monosolvent and cosolvent extractions for milled and unmilled hemp.

FIG. 17 is a line graph of the mass of CBD extracted per hour for monosolvent and ethanol cosolvent extractions for milled and unmilled hemp in a carbon dioxide superfluid extraction. As evident by the data, the use of small amounts of 2% and 3% cosolvent with superfluid extraction results in much higher mass of CBD extracted compared to the use of superfluid monosolvent alone.

Figure 18:
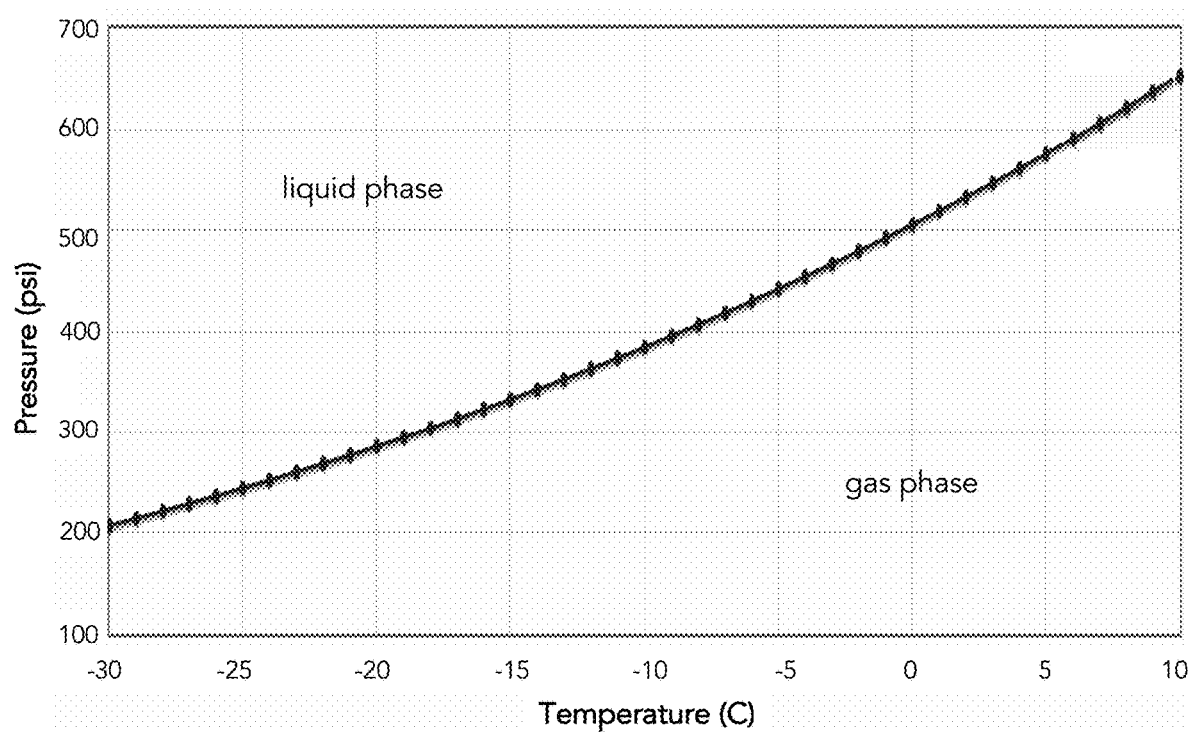
FIG. 18 is a graph of the saturation properties for carbon dioxide by pressure in temperature increments.

FIG. 18 is a graph of the saturation properties for carbon dioxide by pressure in temperature increments.

Figure 19:
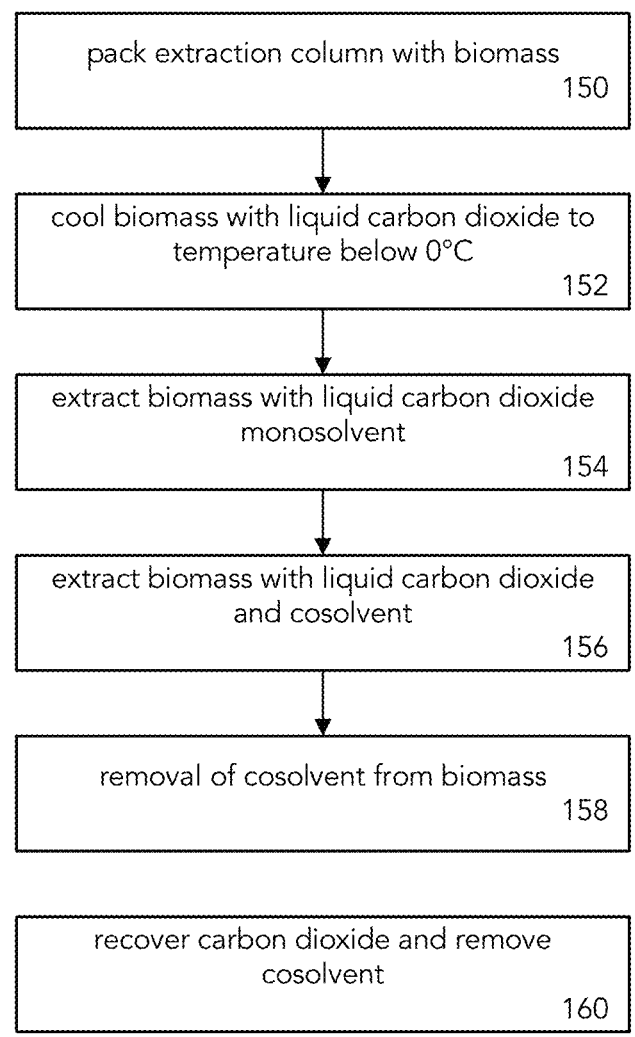
FIG. 19 is a method flowchart for extracting oils from a biomass using a cryogenic carbon dioxide pre-freezing refrigeration step.
Figure 20:
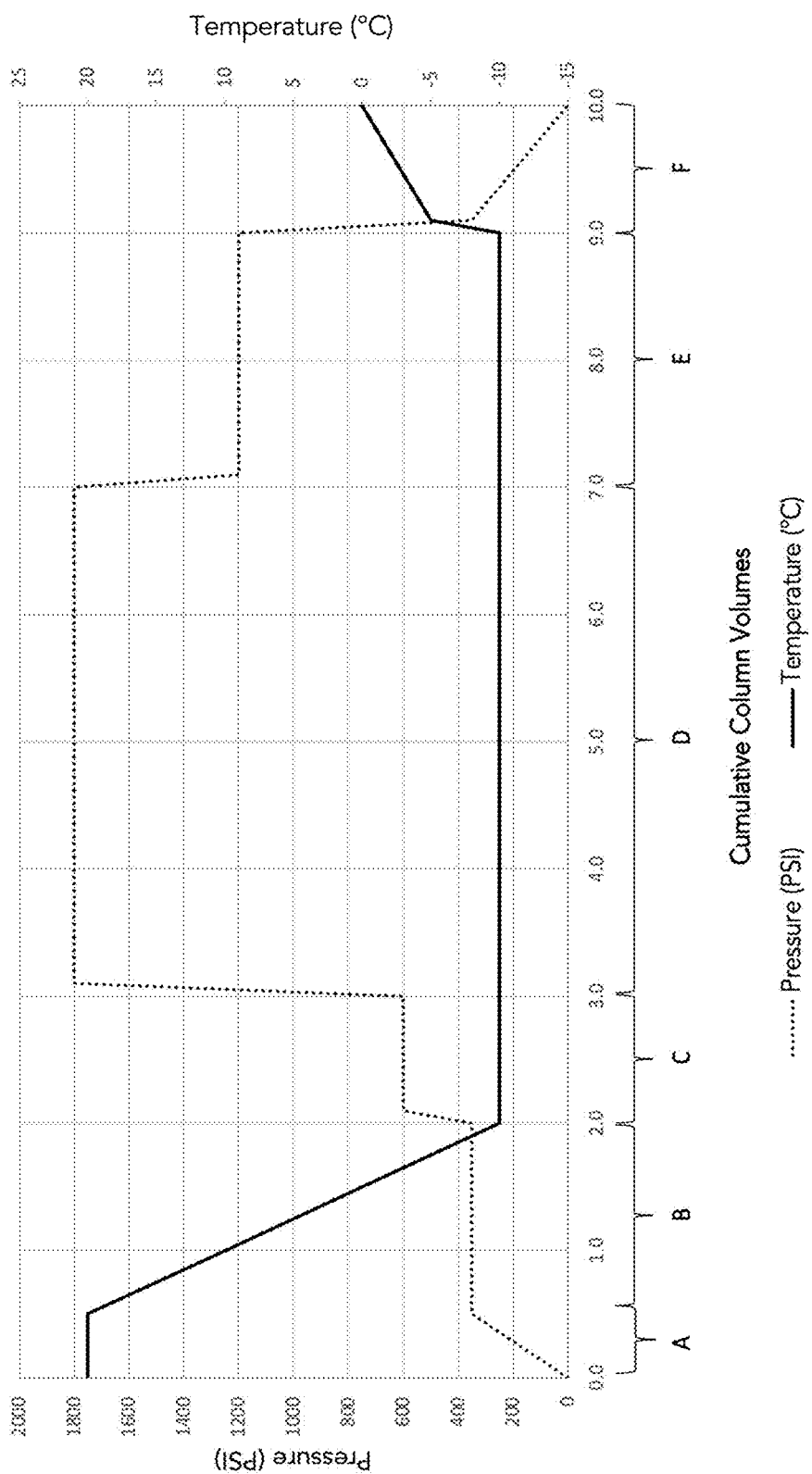
FIG. 20 is a sample extraction profile with column volumes and pressures of carbon dioxide in a process for extracting oils from a biomass using a refrigeration step.

FIG. 19 is a method flowchart for extracting oils from a biomass using a cryo-refrigeration step with the superfluid solvent by way of evaporative cooling. A refrigeration loop system as shown in FIG. 20 is one example system that can be used as a cascade refrigeration system for pre-cooling and cryo-cooling of biomass in this type of superfluid extraction. To prepare for the extraction, the extraction column is packed with biomass 150. The biomass can be any type, such as plant, animal, fungal, or microbiological. Additionally, the biomass can be fresh and unprocessed, dried, freeze-dried, frozen, fresh-frozen, or in any suitable form. The biomass is then cooled with sub-cooled liquid carbon dioxide in the extraction column at relatively low pressures to cryogenically freeze the biomass at a temperature of less than about 0° C. 152. This preliminary cryo-refrigeration step cools and freezes the biomass inside the extraction column, limiting the extraction of chlorophylls and other water soluble compounds, resulting in cleaner $CO_2$ monosolvent and $CO_2$ cosolvent fractions. As observed in the graph in FIG. 18, superfluid $CO_2$ is colder than 0° C. at pressures below 500 psi. It has been found that in a superfluid $CO_2$ method, optimal pressures for this step are below about 500 psi and preferably below about 350 psi. The evaporated gas converted from the supply of liquid carbon dioxide boils at a set temperature based on the physical properties of the superfluid and the controlled pressure of the extraction column. Optimally the extraction column operates in a cascade style system where there is minimal pressure drop between the top of the extraction column and the $CO_2$ recycler. In the optimal system the $CO_2$ recycler maintains the accumulator and liquid supply at saturation properties below 350 psi and below about −10° C. In a configuration where the accumulator is maintained at higher pressures or the liquid carbon dioxide rises to above 0° C. then a heat exchanger can be used to sub cool the liquid carbon dioxide entering the extraction column and a mechanical compressor can be used to maintain the low boiling point pressures of the column to achieve the sub-cooling and freezing objectives. A temperature probe or other sensing instrument in the extraction column indicates when superfluid liquid has reached the top of the column, indicating that all residual heat in the biomass has been removed and the material is frozen. During the cryo-freezing process heat from the biomass vaporizes the $CO_2$, which is recirculated with a refrigeration loop. It has been found that 1-3 column volumes of $CO_2$ in the extraction column is generally sufficient to lower the biomass temperature in the extraction column to less than 0° C. and complete the preliminary cryo-freezing step.

Once the extraction column is cooled the biomass is extracted with sub-cooled liquid $CO_2$ monosolvent 154 of FIG. 19, which is a non-polar solvent, to remove nonpolar and soluble components of the biomass, such as terpenes in the case of cannabis biomass. The biomass is then extracted in a second liquid $CO_2$/cosolvent step 156 to isolate chemical fractions soluble in the liquid $CO_2$/cosolvent. Various process methods of adding the cosolvent to the sub-cooled liquid $CO_2$ can be used, such as in a continuous, gradient or stepwise, depending on the process conditions and biomass type. Once the extraction process is complete the sub-cooled liquid $CO_2$ and cosolvent can be removed from the biomass 158 by treating the biomass with liquid $CO_2$ monosolvent. By removing any residual solvent from the biomass, the biomass waste can be treated as non-toxic waste. During the process the $CO_2$ can be recovered by evaporation from the cosolvent 160 and condensation for recirculation.

FIG. 20 is a sample extraction profile with column volumes and pressures of carbon dioxide in a process for extracting oils from a biomass using a preliminary cryo-refrigeration step. Steps A-F are done in time sequence, shown at the bottom of the graph as measured in column volumes of solvent passed through the extraction column. At step A the extraction column is loaded with biomass and the column is pressurized. Various types and states of biomass can be used in this procedure, including biomass from plant, animal, and fungal origin, in various state ranging from fresh to dry and frozen to non-frozen. In an example, the biomass can be dried, fresh, fresh frozen, and plant and animal material can be broken up, milled, or entirely unprocessed. At step B the extraction column with packed biomass is cryogenically cooled with isobaric boiling of liquid $CO_2$ where the temperature of the biomass is slowly decreasing at constant pressure, and the vaporized $CO_2$ can be directly recovered once the liquid $CO_2$ has done a phase transformation and been vaporized by absorbing heat energy stored in the biomass. As such, the temperature in the column decreases as the biomass cools. Using an in-line condenser and low temperature accumulator the boiled $CO_2$ can be converted back to liquid $CO_2$ at steady pressure until all the biomass in the extraction column has been frozen to a temperature of 0° C. or less. At this temperature the water in the biomass has been frozen, freezing with it water-soluble molecules and other large molecules. Detection of a significant temperature drop at the top of the extraction column is indicative that liquid $CO_2$ has reached the top of the column and that the biomass is frozen. The $CO_2$ pressure at this step must be below 500 psi to freeze trapped water in the biomass, but is preferably about 350 psi or below, or between 300-500 psi. Optimally the biomass and temperature at the discharge of the extraction column is maintained at of below −10 C.

At step C, once the biomass in the extraction column is frozen, the extraction fluid pressure is increased and a first fraction with $CO_2$ monosolvent is removed from the column. $CO_2$ pressures in the monosolvent extraction stage can be in the range of, for example, 400-800 psi, optimally the extraction for terpenes in cannabis is executed near 750 psi, providing the temperature of the biomass is retained at of 0° C. or less. In a cannabinoid extraction process this first fraction contains terpenes, flavonoids, and other small molecules soluble in liquid $CO_2$ monosolvent. One or more column volumes of $CO_2$ monosolvent can be collected from the column depending on the type and state of the biomass, and column volumes can also be extracted at different pressures in different monosolvent fractions. Fractions collected at this step are sent to a separator or cyclone to remove the $CO_2$ and isolate the extractant. One advantage of collecting terpenes in a first $CO_2$ monosolvent extraction is that terpenes have a boiling point similar to cosolvents used in a $CO_2$/cosolvent extraction and are thus difficult to separate from cosolvent once dissolved. Removing terpenes in a first monosolvent extraction enables isolation of terpenes by boiling off of the $CO_2$.

At step D a cosolvent is added to the liquid $CO_2$ and chemical species more soluble in the sub-cooled liquid $CO_2$/cosolvent eluent can be extracted, optionally at a higher solvent pressure. The superfluid pressure in the system can be raised at this point to, for example, between 1500-7500 psi, or preferably between 1500 psi and 2200 psi. Optimally in a cosolvent cannabis extraction application the pressure is increased to near 2000 psi and cosolvent rates in the range of 0.1%-10% and more preferably 3-8% by mass are injected. Greater than 10% cosolvent in carbon dioxide can be used, however higher cosolvent amounts require equipment compensation for high volatility and flammability cosolvents, in addition to stricter regulatory requirements. Moderate pressure ensures that there is good material penetration by the solvent solution for collection of the desired molecules, cannabinoids, and reduced impurities as compared to high pressure liquid or supercritical parameters. Experimentation supports that pressures above 2200 psi for the given flow rates and temperatures showed little improvement in rates of cannabinoid recovery, and higher rates of undesired compound coextraction. In an extraction of cannabis, at this step cannabinoids are eluted in a secondary $CO_2$/cosolvent fraction. The process conditions for the extraction can be changed in % cosolvent, elution (column volume), temperature/pressure, and duration dependent on the available active pharmaceutical ingredient (API) and cosolvent rate, with longer duration extractions required when there is less cosolvent or for monosolvent-only extractions. The cosolvent injection rate can be, for example, 0.1-10% by volume relative to $CO_2$, and can be increased in a stepped, ramped, or flat profile while maintaining column temperature below 0° C., and optimally below −10° C., to obtain oil permeate. It has also been found that cosolvents which are not miscible with water work best with fresh biomass, i.e. biomass that is not dried prior to column packing. Experimentation has shown that solvents like ethyl acetate which have a good ability to dissolve cannabinoids and are immiscible with water at standard conditions produce extracts with lower level of hydrophilic impurities like chlorophyll and carotenoids. It is also advantageous to use these solvents in a cosolvent application further to comply with national fire safety regulations since the $CO_2$ process reduces the total amount of solvent used in the process and thus reduces the building and process room build costs. The extractants obtained using this process are cleaner oils with low wax content and low hydrophilic impurities, reducing the requirement and rigor required for post processing. In addition, the present process results in faster processing times reducing cosolvent and energy use. Post processing with solvents immiscible with water and other hydrophilic solvents allows for reduced purification process by enabling liquid-liquid extraction philosophies suitable for removing said hydrophilic impurities by desorption in a low energy method.

Once all the desired compounds have been removed from the biomass, the biomass can be remediated at step E by switching the solvent back to $CO_2$ monosolvent and flowing monosolvent over the biomass to flush any remaining cosolvent from the column. Liquid $CO_2$ can be recovered at step F in a condensation and depressurization process for recirculation and cosolvent can be removed from disposal, leaving solvent-free biomass which can be disposed of as a non-toxic compost waste.

All publications, patents and patent applications mentioned in this specification are indicative of the level of skill of those skilled in the art to which this invention pertains and are herein incorporated by reference. The reference to any prior art in this specification is not, and should not be taken as, an acknowledgement or any form of suggestion that such prior art forms part of the common general knowledge. The invention being thus described, it will be obvious that the same may be varied in many ways. Such variations are not to be regarded as a departure from the scope of the invention, and all such modifications as would be obvious to one skilled in the art are intended to be included within the scope of the following claims.

We claim:

1. A method for biomass extraction comprising:
   in a cryogenic freezing step before an extraction cycle, cryogenically freezing the biomass in an extraction vessel with liquid carbon dioxide to a temperature of 0° C. or less at a pressure of less than 500 psi by directing liquid carbon dioxide into the bottom of the extraction vessel and transferring heat from the biomass to the liquid carbon dioxide to cause boiling of the liquid carbon dioxide and evaporative cooling of the biomass to a temperature of 0° C. or less until the liquid carbon dioxide level reaches the top of the biomass to freeze any moisture in the biomass;
   in a monosolvent extraction step, extracting the frozen biomass with liquid carbon dioxide monosolvent while maintaining the temperature of the biomass at 0° C. or less to obtain one or more monosolvent fractions;
   in a cosolvent extraction step, extracting the biomass with liquid carbon dioxide and a cosolvent to obtain one or more cosolvent fractions; and
   evaporating the monosolvent fractions and cosolvent fractions to remove the carbon dioxide and obtain an extractant oil.

2. The method of claim 1, wherein the liquid carbon dioxide in the monosolvent extraction step and the cosolvent extraction step is in a subcritical state or supercritical state.

3. The method of claim 1, wherein in the freezing step, the biomass is cooled at a pressure of 400 psi or less with a controlled flow of liquid carbon dioxide through the bottom of the extraction vessel, and wherein the extraction vessel is full of liquid carbon dioxide when the extraction vessel top has a measured vapor temperature below 0° C.

4. The method of claim 1, wherein prior to the cryogenic freezing step the biomass is dry, fresh, or fresh frozen.

5. The method of claim 1, wherein at least one of the monosolvent extraction step and the cosolvent extraction step are carried out at a temperature of −10° C. or less.

6. The method of claim 1, wherein the cryogenic freezing step is performed under isobaric conditions.

7. The method of claim 1, wherein the cosolvent extraction step is carried out at a pressure of between 1500-2200 psi.

8. The method of claim 1, wherein the cosolvent in the cosolvent extraction step is between 0.1-10% by volume in sub-cooled liquid carbon dioxide.

9. The method of claim 1, further comprising dewaxing the extractant oil by one or more of filtration, dewaxing, and nanofiltration.

10. The method of claim 1, further comprising desolvation of the cosolvent fractions.

11. The method of claim 1, further comprising reclaiming the cosolvent.

12. The method of claim 1, further comprising, after the cosolvent extraction step, remediating the biomass by treatment with $CO_2$ monosolvent to remove residual cosolvent.

13. The method of claim 12, wherein the remediated biomass has a cosolvent residual of less than 5000 ppm when removed from the extraction vessel.

14. The method of claim 1, wherein the cosolvent one or more of ethanol, ethyl acetate, isopropyl alcohol, and acetone.

15. The method of claim 1, wherein in the cosolvent extraction step cosolvent is added in an isocratic, step, or linear regime to the liquid carbon dioxide.

16. The method of claim 1, wherein the monosolvent extraction step is carried out at a pressure of between 400-800 psi and the cosolvent extraction step is carried out at a pressure of between 1500-2200 psi.

17. The method of claim 1, wherein during the cryogenic freezing step liquid carbon dioxide is pumped into the extraction vessel at the bottom and carbon dioxide vapor rises to the top of the extraction vessel.

18. The method of claim 1, wherein during the cryogenic freezing step the boiled carbon dioxide is collected in a superfluid condenser and cooled back to recycled liquid carbon dioxide.

19. The method of claim 18, wherein the recycled liquid carbon dioxide is directed back to the extraction vessel.

20. The method of claim 1, wherein a temperature drop to near the condensation temperature of carbon dioxide at the top of extraction vessel during the cryogenic freezing step indicates that the biomass in the extraction vessel is frozen.

* * * * *